United States Patent [19]

Wilde et al.

[11] Patent Number: 5,602,008
[45] Date of Patent: *Feb. 11, 1997

[54] DNA ENCODING A LIVER EXPRESSED CHEMOKINE

[75] Inventors: Craig G. Wilde, Sunnyvale; Phillip R. Hawkins; Olga Bandman, both of Mountain View; Jeffrey J. Seilhamer, Los Altos Hills, all of Calif.

[73] Assignee: Incyte Pharmaceuticals, Inc., Palo Alto, Calif.

[ * ] Notice: The portion of the term of this patent subsequent to Sep. 7, 2014, has been disclaimed.

[21] Appl. No.: 347,492

[22] Filed: Nov. 29, 1994

[51] Int. Cl.$^6$ .......................... C07K 14/52; C12N 15/19
[52] U.S. Cl. ................. 435/69.5; 435/172.3; 435/252.3; 435/320.1; 435/325; 435/358; 435/366; 435/348; 536/23.1; 536/23.5; 530/300; 935/11; 935/22; 935/66
[58] Field of Search ................. 536/23.1, 23.5; 435/69.5, 172.3, 240.1, 252.3, 320.1; 935/11, 22, 66; 530/300

[56] References Cited

PUBLICATIONS

Lipes et al., "Identification, cloning, and characterization of an immune activation gene," Proceedings of the National Academy of Sciences USA, vol. 85, pp. 9704–9708 (Dec. 1988).

Matoba et al., "The Addition of 5'–coding information to a 3'–directed cDNA llibrary improves analysis of gene expression," Gene, vol. 145, pp. 199–207 (1994).

Jan Vilcek, et al., Immunology of Cytokines, *The Cytokine Handbook*, Academic Press, Copyright 1991, Chapter 1, pp. 1–17.

Alan R. Shaw, Molecular Biology of Cytokines, *The Cytokine Handbook*, Academic Press, Copyright 1991, Chapter 2, pp. 20–46.

Jacques Banchereau, Interleukin–4, *The Cytokine Handbook*, Academic Press, Copyright 1991, Chapter 6, pp. 120–148.

Thomas J. Schall, The Chemokines, *The Cytokine Handbook*, Academic Press, 1994, Sep. 19–20, 1994, Second Edition, pp. 180–272.

Opdenakker et al. (1994) Genomics vol. 21, pp. 403–408.
Yoshida et al. (1995) FEBS Letters vol. 360 pp. 155–159.

*Primary Examiner*—John Ulm
*Assistant Examiner*—Prema Mertz
*Attorney, Agent, or Firm*—Incyte Pharmaceuticals, Inc.; Barbara J. Luther

[57] ABSTRACT

The present invention provides nucleotide and amino acid sequences that identify and encode novel expressed chemokines (ECs) from liver and pituitary gland tissues. The present invention also provides for antisense molecules to the nucleotide sequences which encode ECs, expression vectors for the production of purified ECs, antibodies capable of binding specifically to ECs, hybridization probes or oligonucleotides for the detection of EC-encoding nucleotide sequences, genetically engineered host cells for the expression of ECs, diagnostic tests for inflammation or disease based on on EC-encoding nucleic acid molecules or antibodies capable of binding specifically to ECs, pharmaceutical compositions to treat inflammation or disease based on EC-encoding nucleic acid molecules or antibodies capable of binding specifically to ECs.

5 Claims, 11 Drawing Sheets

```
                9              18              27              36              45              54
5' ATG AAG GTC TCC GAG GCT GCC CTG TCT CTC CTT GTC CTC ATC CTT ATC ATT ACT
   M   K   V   S   E   A   A   L   S   L   L   V   L   I   L   I   I   T 63              72              81              90              99             108
   TCG GCT TCT CGC AGC CAG CCA AAA GTT CCT GAG TGG GTG AAC ACC CCA TCC ACC
   S   A   S   R   S   Q   P   K   V   P   E   W   V   N   T   P   S   T 117             126             135             144             153             162
   TGC TGC CTG AAG TAT TAT GAG AAA GTG TTG CCA AGG AGA CTA GTG GTG GGA TAC
   C   C   L   K   Y   Y   E   K   V   L   P   R   R   L   V   V   G   Y 171             180             189             198             207             216
   AGA AAG GCC CTC AAC TGT CAC CTG CCA GCA ATC ATC TTC GTC ACC AAG AGG AAC
   R   K   A   L   N   C   H   L   P   A   I   I   F   V   T   K   R   N 225             234             243             252             261             270
   CGA GAA GTC TGC ACC AAC CCC AAT GAC GAC TGG GTC CAA GAG TAC ATC AAG GAT
   R   E   V   C   T   N   P   N   D   D   W   V   Q   E   Y   I   K   D 279             288             297             306             315             324
   CCC AAC CTA CCT TTG CTG CCT ACC AGG AAC TTG TCC ACG GTT AAA ATT ATT ACA
   P   N   L   P   L   L   P   T   R   N   L   S   T   V   K   I   I   T 333             342             351             360
   GCA AAG AAT GGT CAA CCC CAG CTC CTC AAC TCC CAG TGA   3'
   A   K   N   G   Q   P   Q   L   L   N   S   Q   *
```

FIG. 1

| Analysis | Whole Protein |
|---|---|
| Molecular Weight | 13600.30 m.w. |
| Length | 120 |
| 1 microgram = | 73.528 pMoles |
| Molar Extinction coefficient | 16980±5% |
| 1 A(280) = | 0.80 mg/ml |
| Isoelectric Point | 9.57 |
| Charge at pH 7 | 7.96 |

Whole Protein Composition Analysis

| Amino Acid(s) | Number count | % by weight | % by frequency |
|---|---|---|---|
| Charged (RKHYCDE) | 33 | 32.65 | 27.50 |
| Acidic (DE) | 8 | 7.29 | 6.67 |
| Basic (KR) | 16 | 16.52 | 13.33 |
| Polar (NCQSTY) | 38 | 31.17 | 31.67 |
| Hydrophobic (AILFWV) | 44 | 34.95 | 36.67 |
| A  Ala | 6 | 3.14 | 5.00 |
| C  Cys | 4 | 3.04 | 3.33 |
| D  Asp | 3 | 2.54 | 2.50 |
| E  Glu | 5 | 4.75 | 4.17 |
| F  Phe | 1 | 1.08 | 0.83 |
| G  Gly | 2 | 0.84 | 1.67 |
| H  His | 1 | 1.01 | 0.83 |
| I  Ile | 8 | 6.66 | 6.67 |
| K  Lys | 9 | 8.48 | 7.50 |
| L  Leu | 16 | 13.32 | 13.33 |
| M  Met | 1 | 0.96 | 0.83 |
| N  Asn | 9 | 7.55 | 7.50 |
| P  Pro | 10 | 7.14 | 8.33 |
| Q  Gln | 5 | 4.71 | 4.17 |
| R  Arg | 7 | 8.04 | 5.83 |
| S  Ser | 8 | 5.12 | 6.67 |
| T  Thr | 8 | 5.95 | 6.67 |
| V  Val | 11 | 8.02 | 9.17 |
| W  Trp | 2 | 2.74 | 1.67 |
| Y  Tyr | 4 | 4.80 | 3.33 |
| B  Asx | 0 | 0.00 | 0.00 |
| Z  Glx | 0 | 0.00 | 0.00 |
| X  Xxx | 0 | 0.00 | 0.00 |
| .  Ter | 0 | 0.00 | 0.00 |

FIG. 2

```
                   9              18              27              36              45              54
5' ATG TGC TGT ACC AAG AGT TTG CTC CTG GCT GCT TTG ATG TCA GTG CTG CTA CTC
    M   C   C   T   K   S   L   L   L   A   A   L   M   S   V   L   L   L 63              72              81              90              99             108
   CAC CTC TGC GGC GAA TCA GAA GCA GCA AGC AAC TTT GAC TGC TGT CTT GGA TAC
    H   L   C   G   E   S   E   A   A   S   N   F   D   C   C   L   G   Y 117             126             135             144             153             162
   ACA GAC CGT ATT CTT CAT CCT AAA TTT ATT GTG GGC TTC ACA CGG CAG CTG GCC
    T   D   R   I   L   H   P   K   F   I   V   G   F   T   R   Q   L   A 171             180             189             198             207             216
   AAT GAA GGC TGT GAC ATC AAT GCT ATC ATC TTT CAC ACA AAG AAA AAG TTG TCT
    N   E   G   C   D   I   N   A   I   I   F   H   T   K   K   K   L   S 225             234             243             252             261             270
   GTG TGC GCA AAT CCA AAA CAG ACT TGG GTG AAA TAT ATT GTG CGT CTC CTC AGT
    V   C   A   N   P   K   Q   T   W   V   K   Y   I   V   R   L   L   S 279             288
   AAA AAA GTC AAG AAC ATG TAA 3'
    K   K   V   K   N   M   *
```

FIG. 4

| Analysis | Whole Protein |
|---|---|
| Molecular Weight | 10762.90 m.w. |
| Length | 96 |
| 1 microgram = | 92.912 pMoles |
| Molar Extinction coefficient | 9090±5% |
| 1 A(280) = | 1.18 mg/ml |
| Isoelectric Point | 8.95 |
| Charge at pH 7 | 7.19 |

Whole Protein Composition Analysis

| Amino Acid(s) | Number count | % by weight | % by frequency |
|---|---|---|---|
| Charged (RKHYCDE) | 31 | 36.64 | 32.29 |
| Acidic (DE) | 6 | 6.81 | 6.25 |
| Basic (KR) | 13 | 16.27 | 13.54 |
| Polar (NCQSTY) | 27 | 26.98 | 28.12 |
| Hydrophobic (AILFWV) | 38 | 38.38 | 39.58 |
| A Ala | 7 | 4.62 | 7.29 |
| C Cys | 7 | 6.71 | 7.29 |
| D Asp | 3 | 3.21 | 3.12 |
| E Glu | 3 | 3.60 | 3.12 |
| F Phe | 4 | 5.47 | 4.17 |
| G Gly | 4 | 2.12 | 4.17 |
| H His | 3 | 3.82 | 3.12 |
| I Ile | 6 | 6.31 | 6.25 |
| K Lys | 10 | 11.91 | 10.42 |
| L Leu | 14 | 14.72 | 14.58 |
| M Met | 3 | 3.66 | 3.12 |
| N Asn | 5 | 5.30 | 5.21 |
| P Pro | 2 | 1.80 | 2.08 |
| Q Gln | 2 | 2.38 | 2.08 |
| R Arg | 3 | 4.35 | 3.12 |
| S Ser | 6 | 4.86 | 6.25 |
| T Thr | 5 | 4.70 | 5.21 |
| V Val | 6 | 5.52 | 6.25 |
| W Trp | 1 | 1.73 | 1.04 |
| Y Tyr | 2 | 3.03 | 2.08 |
| B Asx | 0 | 0.00 | 0.00 |
| Z Glx | 0 | 0.00 | 0.00 |
| X Xxx | 0 | 0.00 | 0.00 |
| Ter | 0 | 0.00 | 0.00 |

FIG. 5

```
             9              18              27              36              45              54
5' ATG AAG ATC TCC GTG GCT GCC ATT CCC TTC TTC CTC CTC ATC ACC ATC GCC CTA
   M   K   I   S   V   A   A   I   P   F   F   L   L   I   T   I   A   L 63              72              81              90              99             108
   GGG ACC AAG ACT GAA TCC TCC TCA CGG GGA CCT TAC CAC CCC TCA GAG TGC TGC
   G   T   K   T   E   S   S   S   R   G   P   Y   H   P   S   E   C   C 117             126             135             144             153             162
   TTC ACC TAC ACT ACC TAC AAG ATC CCG CGT CAG CGG ATT ATG GAT TAC TAT GAG
   F   T   Y   T   T   Y   K   I   P   R   Q   R   I   M   D   Y   Y   E 171             180             189             198             207             216
   ACC AAC AGC CAG TGC TCC AAG CCC GGA ATT GTC TTC ATC ACC AAA AGG GGC CAT
   T   N   S   Q   C   S   K   P   G   I   V   F   I   T   K   R   G   H 225             234             243             252             261             270
   TCC GTC TGT ACC AAC CCC AGT GAC AAG TGG GTC CAG GAC TAT ATC AAG GAC ATG
   S   V   C   T   N   P   S   D   K   W   V   Q   D   Y   I   K   D   M

279
   AAG GAG AAC TGA 3'
   K   E   N   *
```

FIG. 7

| Analysis | Whole Protein |
| --- | --- |
| Molecular Weight | 10678.70 m.w. |
| Length | 93 |
| 1 microgram = | 93.644 pMoles |
| Molar Extinction coefficient | 13850±5% |
| 1 A(280) = | 0.77 mg/ml |
| Isoelectric Point | 8.73 |
| Charge at pH 7 | 4.12 |

Whole Protein Composition Analysis

| Amino Acid(s) | Number count | % by weight | % by frequency |
| --- | --- | --- | --- |
| Charged (RKHYCDE) | 32 | 40.21 | 34.41 |
| Acidic (DE) | 8 | 9.15 | 8.60 |
| Basic (KR) | 12 | 15.46 | 12.90 |
| Polar (NCQSTY) | 34 | 35.70 | 36.56 |
| Hydrophobic (AILFWV) | 24 | 25.69 | 25.81 |
| A Ala | 3 | 2.00 | 3.23 |
| C Cys | 4 | 3.87 | 4.30 |
| D Asp | 4 | 4.31 | 4.30 |
| E Glu | 4 | 4.84 | 4.30 |
| F Phe | 4 | 5.51 | 4.30 |
| G Gly | 4 | 2.14 | 4.30 |
| H His | 2 | 2.57 | 2.15 |
| I Ile | 9 | 9.54 | 9.68 |
| K Lys | 8 | 9.60 | 8.60 |
| L Leu | 3 | 3.18 | 3.23 |
| M Met | 3 | 3.69 | 3.23 |
| N Asn | 3 | 3.21 | 3.23 |
| P Pro | 6 | 5.46 | 6.45 |
| Q Gln | 3 | 3.60 | 3.23 |
| R Arg | 4 | 5.85 | 4.30 |
| S Ser | 9 | 7.34 | 9.68 |
| T Thr | 9 | 8.52 | 9.68 |
| V Val | 4 | 3.71 | 4.30 |
| W Trp | 1 | 1.74 | 1.08 |
| Y Tyr | 6 | 9.17 | 6.45 |
| B Asx | 0 | 0.00 | 0.00 |
| Z Glx | 0 | 0.00 | 0.00 |
| X Xxx | 0 | 0.00 | 0.00 |
| . Ter | 0 | 0.00 | 0.00 |

FIG. 8

DNA ENCODING A LIVER EXPRESSED CHEMOKINE

CROSS-REFERENCE TO RELATED APPLICATIONS

This application is related to co-pending applications Ser. Nos. 08/303,241 (liver) and 08/320,011 (pituitary gland).

BACKGROUND OF THE INVENTION

Leukocytes including monocytes, macrophages, basophils, and eosinophils play important roles in the pathological mechanisms initiated by T and/or B lymphocytes. Macrophages, in particular, produce powerful oxidants and proteases which contribute to tissue destruction and secrete a range of cytokines which recruit and activate other inflammatory cells.

The investigation of the critical, regulatory processes by which white cells proceed to their appropriate destination and interact with other cells is underway. The current model of leukocyte movement or trafficking from the blood to injured or inflamed tissues comprises the following steps. The first step is the rolling adhesion of the leukocyte along the endothelial cells of the blood vessel wall. This movement is mediated by transient interactions between selectins and their ligands. A second step involves cell activation which promotes a more stable leukocyte-endothelial cell interaction mediated by the integrins and their ligands. This stronger, more stable adhesion precipitates the final steps-leukocyte diapedesis and extravasation into the tissues.

The chemokine family of polypeptide cytokines, also known as intercrines, possesses the cellular specificity required to explain leukocyte trafficking in different inflammatory situations. First, chemokines mediate the expression of particular adhesion molecules on endothelial cells; and second, they generate gradients of chemoattractant factors which activate specific cell types. In addition, the chemokines stimulate the proliferation of specific cell types and regulate the activation of cells which bear specific receptors. Both of these activities demonstrate a high degree of target cell specificity.

The chemokines are small polypeptides, generally about 70–100 amino acids (aa) in length, 8–11 kD in molecular weight and active over a 1–100 ng/ml concentration range. Initially, they were isolated and purified from inflamed tissues and characterized relative to their bioactivity. More recently, chemokines have been discovered through molecular cloning techniques and characterized by structural as well as functional analysis.

The chemokines are related through a four cysteine motif which is based primarily on the spacing of the first two cysteine residues in the mature molecule. Currently the chemokines are assigned to one of two families, the C—X—C chemokines ($\alpha$) and the C—C chemokines ($\beta$). Although exceptions exist, the C—X—C chemokines generally activate neutrophils and fibroblasts while the C—C chemokines act on a more diverse group of target cells which include monocytes/macrophages, basophils, eosinophils, T lymphocytes and others. The known chemokines of both families are synthesized by many diverse cell types as reviewed in Thomson A. (1994) The Cytokine Handbook, 2 d Ed. Academic Press, N.Y. The two groups of chemokines will be described in turn.

At this time, the C—C chemokines number fewer than the C—X—C chemokines, and they appear to have less N-terminal processing. A brief description of the known human (and/or murine) C—C chemokines follows. The macrophage inflammatory proteins alpha and beta (MIP-1$\alpha$ and $\beta$) were first purified from stimulated mouse macrophage cell line and elicited an inflammatory response when injected into normal tissues. At least three distinct and non-allelic genes encode human MIP-1$\alpha$ and seven such genes encode MIP-1$\beta$.

MIP-1$\alpha$ and MIP-1$\beta$ consist of 68–69 aa which are about 70% identical in their acidic, mature secreted forms. They are both expressed in stimulated T cells, B cells and monocytes in response to mitogens, anti-CD3 and endotoxin, and both polypeptides bind heparin. While both molecules stimulate monocytes, MIP-1$\alpha$ chemoattracts the CD-8 subset of T lymphocytes and eosinphils, while MIP-1$\beta$ chemoattracts the CD-4 subset of T lymphocytes. In mouse, these proteins are known to stimulate myelopoiesis.

I-309 was cloned from a human $\gamma$-$\delta$ T cell line and shows 42% aa identity to T cell activation gene 3 (TCA3) cloned from mouse. There is considerable nucleotide homology between the 5' flanking regions of these two proteins, and they share an extra pair of cysteine residues not found in other chemokines. Such similarities suggest I-309 and TCA3 are species homologs which have diverged in sequence and function.

RANTES is another C—C chemokine which is expressed in T cells (but not B cells), in platelets, in some tumor cell lines, and in stimulated rheumatoid synovial fibroblasts. In the latter, it is regulated by interleukins-1 and -4, transforming nerve factor and interferon-$\gamma$. The cDNA cloned from T cells encodes a basic 8 kD protein which lacks N-linked glycosylation and is able to affect lymphocytes, monocytes, basophils and eosinophils. The expression of RANTES mRNA is substantially reduced following T cell stimulation.

Monocyte chemotactic protein (MCP-1) is a 76 aa protein which appears to be expressed in almost all cells and tissues upon stimulation by a variety of agents. The targets of MCP-1, however, are limited to monocytes and basophils in which it induces a MCP-1 receptor: G protein-linked calcium flux (Charo I, personal communication). Two other related proteins (MCP-2 and MCP-3) were purified from a human osteosarcoma cell line. MCP-2 and MCP-3 have 62% and 73% aa identity, respectively, with MCP-1 and share its chemoattractant specificity for monocytes.

Current techniques for diagnosis of abnormalities in the inflamed or diseased tissues mainly rely on observation of clinical symptoms or serological analyses of body tissues or fluids for hormones, polypeptides or various metabolites. Patients often manifest no clinical symptoms at early stages of disease or tumor development. Furthermore, serological analyses do not always differentiate between invasive diseases and genetic syndromes which have overlapping or very similar ranges. Thus, development of new diagnostic techniques comprising small molecules such as the expressed chemokines are important to provide for early and accurate diagnoses, to give a better understanding of molecular pathogenesis, and to use in the development of effective therapies.

The chemokine molecules were reviewed in Schall TJ (1994) Chemotactic Cytokines: Targets for Therapeutic Development. International Business Communications, Southborough Mass. pp 180–270; and in Paul WE (1993) Fundamental Immunology, 3 rd Ed. Raven Press, N.Y. pp 822–826.

SUMMARY OF THE INVENTION

The subject invention provides a nucleotide sequence which uniquely encodes a novel human protein from normal liver tissue. The new gene, which is known as liver expressed chemokine 1, or Ivec-1 (Incyte Clone No. 87825), encodes a polypeptide designated LVEC-1, of the C—C chemokine family. The invention also comprises diagnostic tests for inflammatory conditions which include the steps of testing a sample or an extract thereof with Ivec-1 DNA, oligomers or fragments thereof. Aspects of the invention include the antisense DNAs of Ivec-1; cloning or expression vectors containing Ivec-1; host cells or organisms transformed with expression vectors containing Ivec-1; a method for the production and recovery of purified LVEC-1 from host cells; and purified LVEC-1.

The subject invention provides a nucleotide sequence which uniquely encodes a novel human protein from normal liver tissue and T and B cell hybrids. The new gene, which is known as liver expressed chemokine 2, or Ivec-2 (Incyte Clone Nos. 88564), encodes a polypeptide designated LVEC-2, of the C—C chemokine family. The invention also comprises diagnostic tests for inflammatory conditions which include the steps of testing a sample or an extract thereof with Ivec-2 DNA, oligomers or fragments thereof. Aspects of the invention include the antisense DNAs of Ivec-2; cloning or expression vectors containing Ivec-2; host cells or organisms transformed with expression vectors containing Ivec-2; a method for the production and recovery of purified LVEC-2 from host cells; and purified LVEC-2.

The subject invention provides a nucleotide sequence which uniquely encodes a novel human protein from normal pituitary gland and liver. The new gene, which is known as pituitary gland expressed chemokine, or pgec (Incyte Clone Nos. 111571), encodes a polypeptide designated PGEC, of the C—C chemokine family. The invention also comprises diagnostic tests for inflammatory conditions which include the steps of testing a sample or an extract thereof with pgec DNA, oligomers or fragments thereof. Aspects of the invention include the antisense DNAs of PGEC; cloning or expression vectors containing pgec; host cells or organisms transformed with expression vectors containing pgec; a method for the production and recovery of purified PGEC from host cells; and purified PGEC.

DESCRIPTION OF THE FIGURES

FIG. 1 displays the nucleotide sequence for Ivec-1 (SEQ ID NO: 1) and the predicted amino acid (aa) sequence of the liver expressed chemokine 1, LVEC-1 (SEQ ID NO: 2).

FIG. 2 provides an analysis of biochemical characteristics of LVEC-1 based on the predicted aa sequence and composition.

FIG. 4 displays the nucleotide sequence of Ivec-2 and the predicted aa sequence of the liver expressed chemokine, LVEC-2.

FIG. 5 provides an analysis of biochemical characteristics of LVEC-2 based on the predicted aa sequence and composition.

FIG. 7 displays the nucleotide sequence of pgec and the predicted aa sequence of the liver expressed chemokine, PGEC.

FIG. 8 provides an analysis of biochemical characteristics of PGEC based on the predicted aa sequence and composition.

DETAILED DESCRIPTION OF THE INVENTION

Definitions

Figure 3:
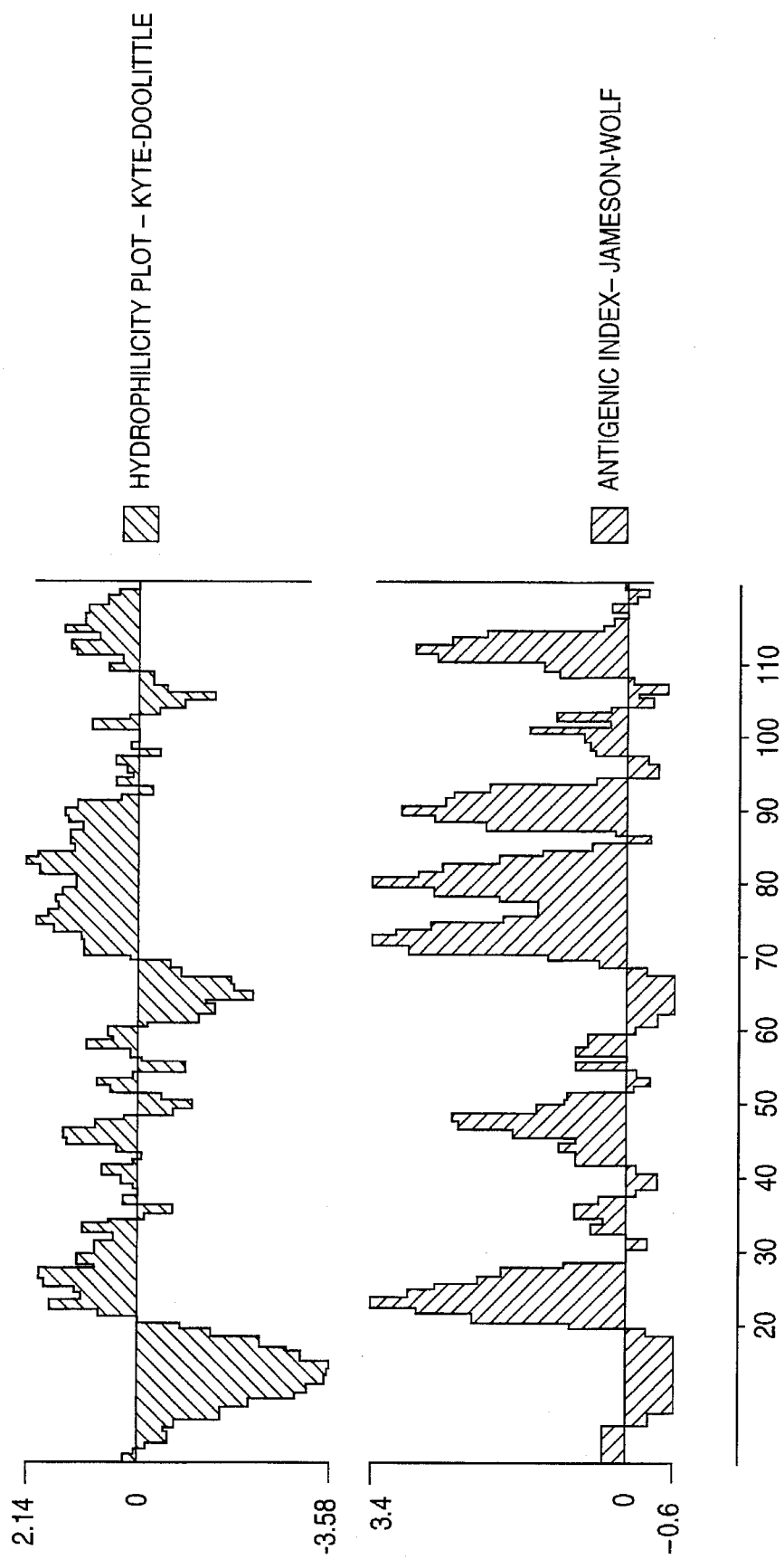
FIG. 3 displays an analysis of hydrophobicity and immunogenic characteristics of LVEC-1 based on the predicted aa sequence and composition.
Figure 6:
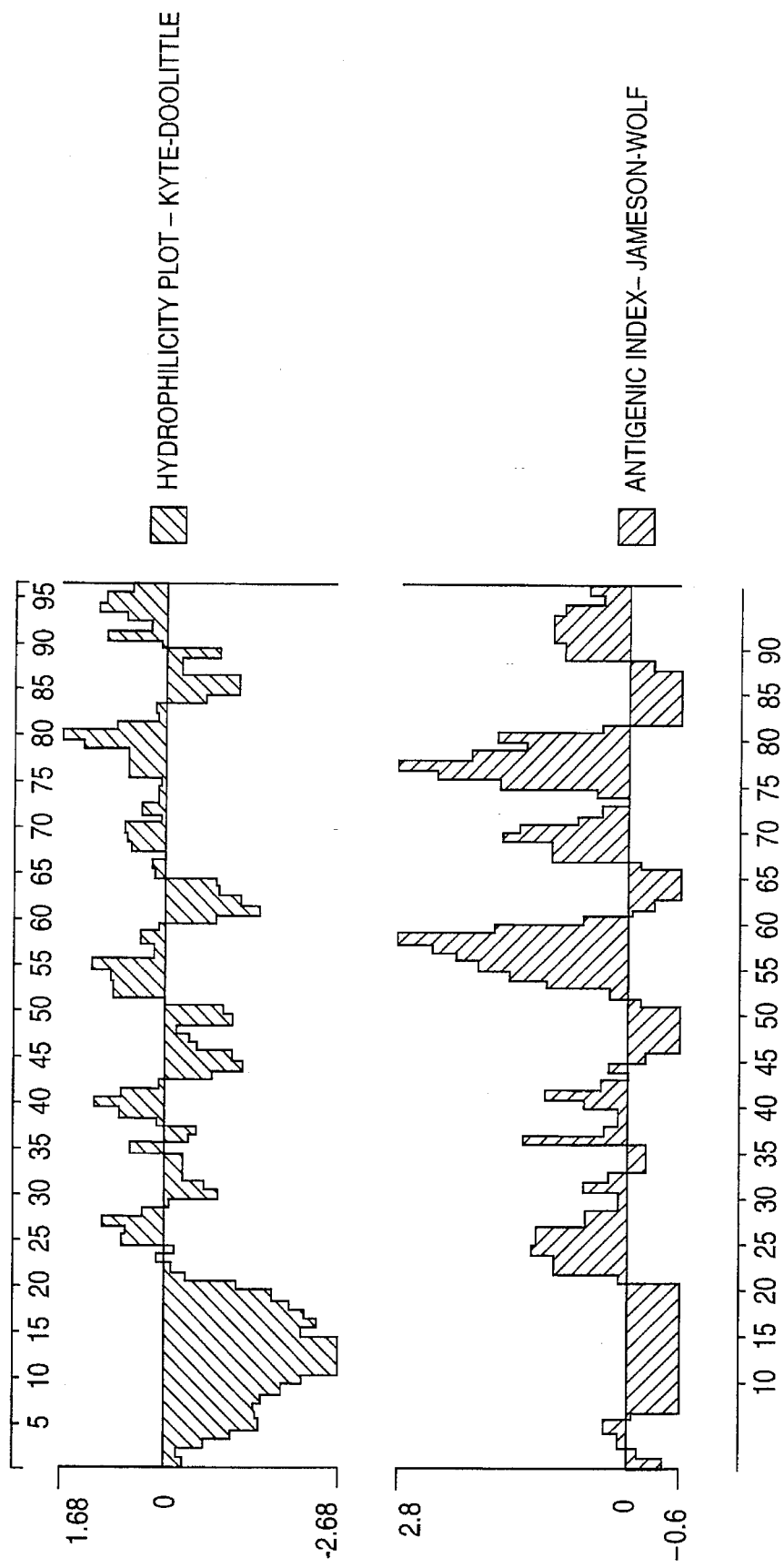
FIG. 6 displays an analysis of hydrophobicity and immunogenic characteristics of LVEC-2 based on the predicted aa sequence and composition.
Figure 9:
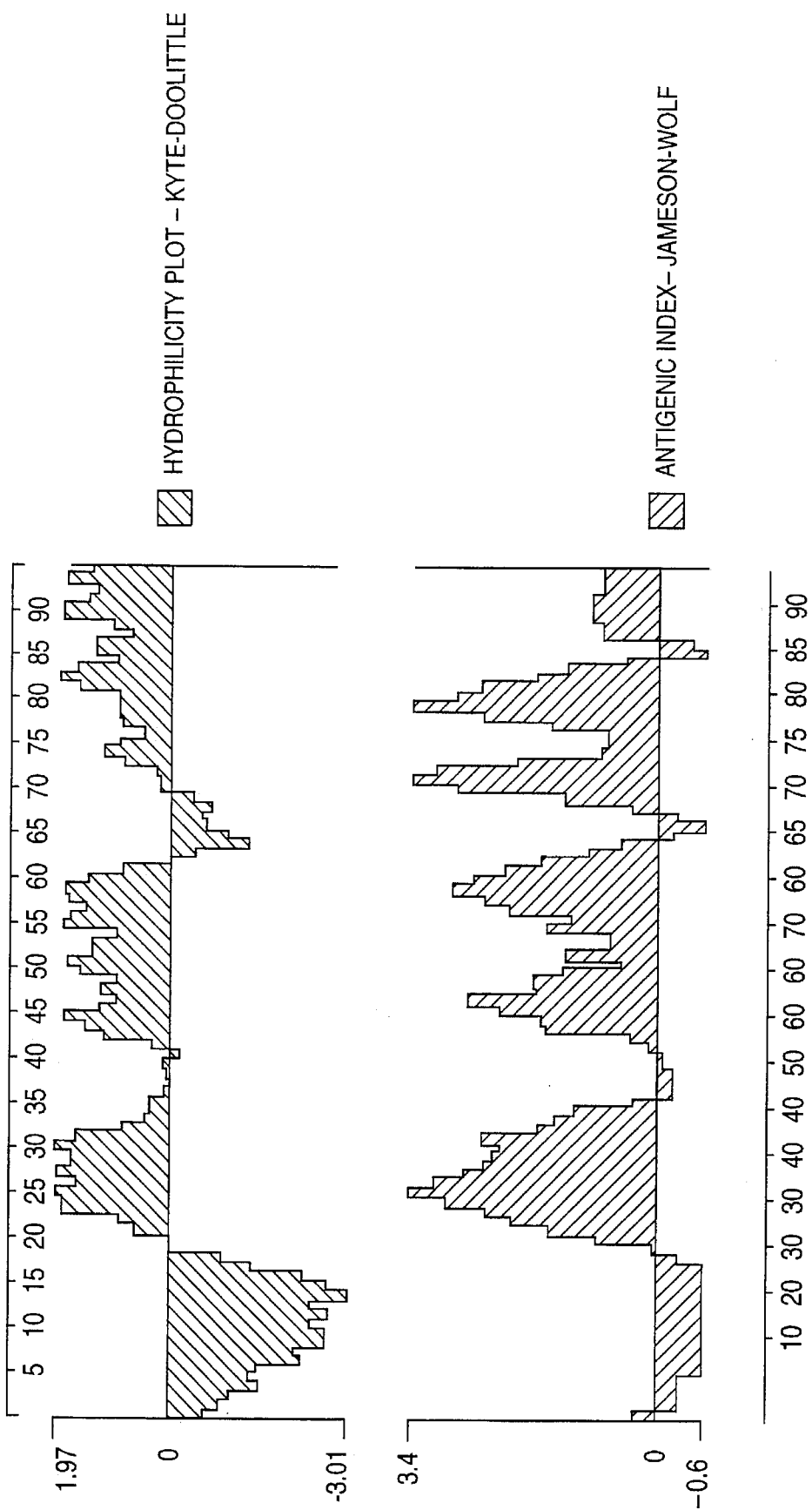
FIG. 9 displays an analysis of hydrophobicity and immunogenic characteristics of PGEC based on the predicted aa sequence and composition.
Figure 10:
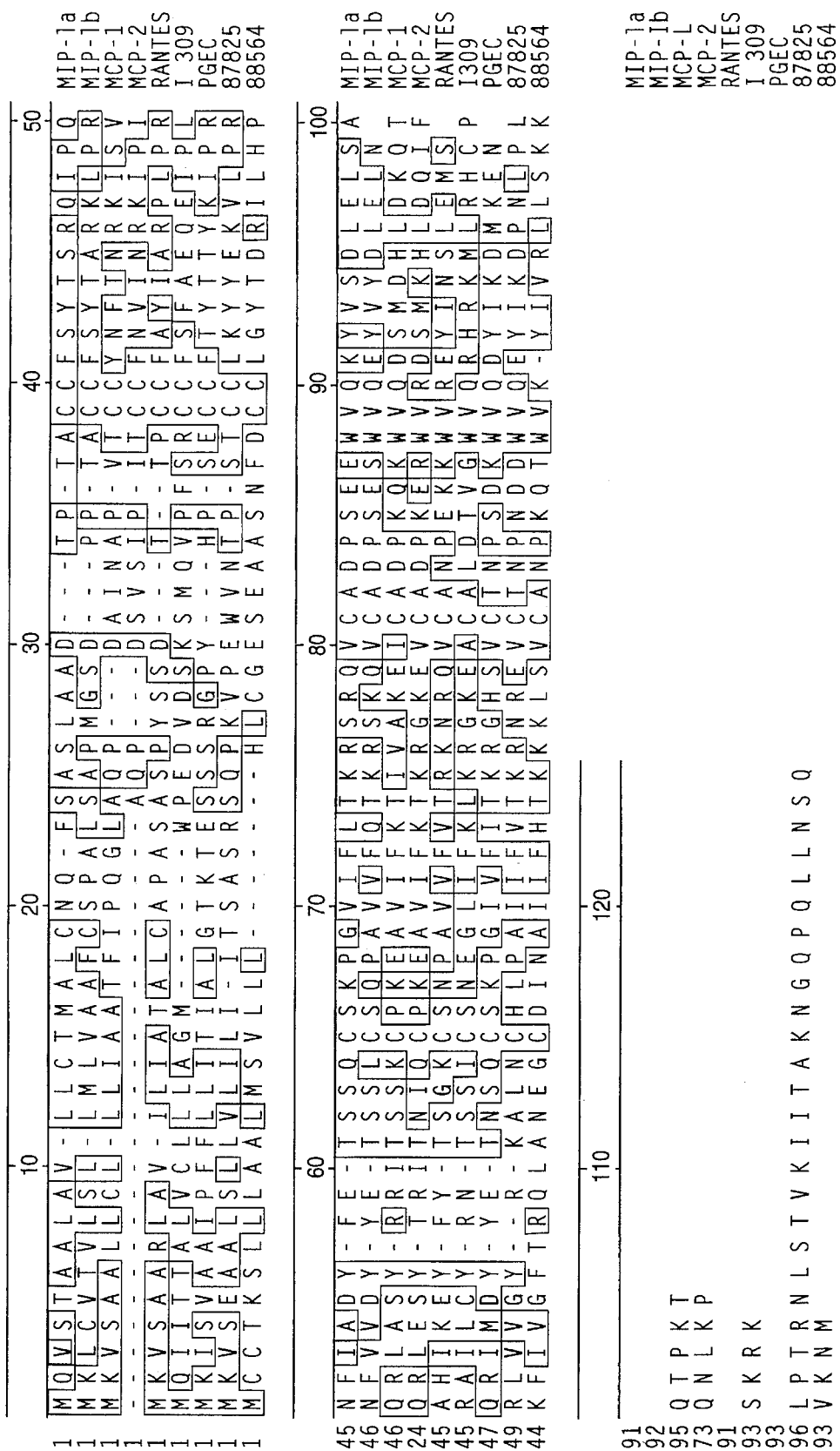
FIG. 10 shows the aa alignment of LVEC-1, LVEC-2, and PGEC with other human chemokines of the C—C family (I-309, SEQ ID NO: 7; MCP-1, SEQ ID NO: 8; MCP-2, SEQ ID NO: 9; MIP-1α, SEQ ID NO: 10; MIP 1β, SEQ ID NO: 11; and Rantes, SEQ ID NO: 12). Alignments shown were produced using the multisequence alignment program of DNAstar software.
Figure 11:
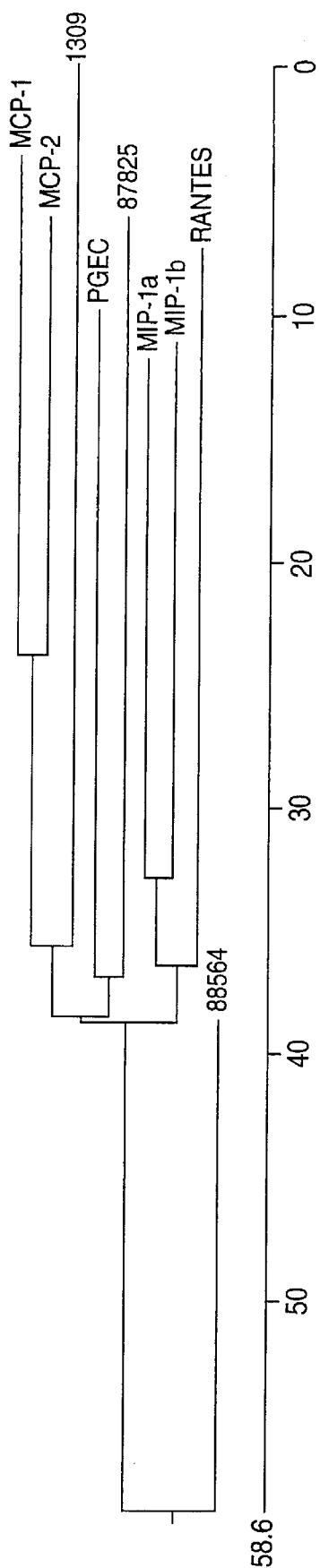
FIG. 11 shows a relatedness tree of human CC chemokines. The phylogenetic tree was generated by phylogenetic tree program of DNAstar software using the Clustal method with the PAM250 residue weight table.

As used herein, "expressed chemokine" (EC) refers to a polypeptide, a naturally occurring EC or active fragments thereof, which is encoded by an mRNA transcribed from the EC cDNA of a particular Seq ID No.

"Active" refers to those forms of EC which retain the biologic and/or immunologic activities of naturally occurring EC.

"Naturally occurring ECs" refers to ECs produced by human cells that have not been genetically engineered and specifically contemplates various EC forms arising from post-translational modifications of the polypeptide including but not limited to acetylation, carboxylation, glycosylation, phosphorylation, lipidation and acylation.

"Derivative" refers to polypeptides derived from naturally occurring EC by chemical modifications such as ubiquitination, labeling (e.g., with radionuclides, various enzymatic modifications), pegylation (derivatization with polyethylene glycol) or by insertion or substitution by chemical synthesis of aa such as ornithine, which do not normally occur in human proteins.

"Recombinant variant" refers to any polypeptide differing from naturally occurring EC by aa insertions, deletions, and substitutions, created using recombinant DNA techniques. Guidance in determining which aa residues may be replaced, added or deleted without abolishing activities of interest, cell adhesion and chemotaxis, may be found by comparing the sequence of the particular EC with that of homologous cytokines and minimizing the number of aa sequence changes made in regions of high homology.

Preferably, aa substitutions are the result of replacing one aa with another aa having similar structural and/or chemical properties, such as the replacement of a leucine with an isoleucine or valine, an aspartate with a glutamate, or a threonine with a serine, i.e., conservative aa replacements. Insertions or deletions are typically in the range of about 1 to 5 aa. The variation allowed may be experimentally determined by systematically making insertions, deletions, or substitutions of aa in EC using recombinant DNA techniques and assaying the resulting recombinant variants for activity.

Where desired, a "signal or leader sequence" can direct the polypeptide through the membrane of a cell. Such a sequence may be naturally present on the polypeptides of the present invention or provided from heterologous protein sources by recombinant DNA techniques.

A polypeptide "fragment," "portion," or "segment" is a stretch of aa residues of at least about 5 amino acids, often at least about 7 aa, typically at least about 9 to 13 aa, and, in various embodiments, at least about 17 or more aa. To be active, an EC polypeptide must have sufficient length to display biologic and/or immunologic activity.

An "oligonucleotide" or polynucleotide "fragment", "portion," or "segment" is a stretch of nucleotide residues which is long enough to use in polymerase chain reaction (PCR) or various hybridization procedures to amplify or simply reveal related parts of mRNA or DNA molecules.

The present invention includes purified EC polypeptides from natural or recombinant sources, cells transformed with recombinant nucleic acid molecules encoding ECs. Various methods for the isolation of the EC polypeptides may be accomplished by procedures well known in the art. For example, such polypeptides may be purified by immunoaffinity chromatography by employing the antibodies provided by the present invention. Various other methods of protein purification well known in the art include those described in Deutscher M (1990) Methods in Enzymology Vol. 182, Academic Press, San Diego; and Scopes R (1982) Protein Purification: Principles and Practice. Springer-Verlag, New York, both incorporated herein by reference.

"Recombinant" may also refer to a polynucleotide which encodes an EC and is prepared using recombinant DNA techniques. The DNA which encodes an EC may also include allelic or recombinant variants and mutants thereof.

"Oligonucleotides" or "nucleic acid probes" are prepared based on the cDNA sequence which encodes an EC provided by the present invention. Oligonucleotides comprise portions of the DNA sequence having at least about 15 nucleotides, usually at least about 20 nucleotides. NuCleic acid probes comprise portions of the sequence having fewer nucleotides than about 6 kb, usually fewer than about 1 kb. After appropriate testing to eliminate false positives, these probes may be used to determine whether mRNA encoding a particular EC is present in a cell or tissue or to isolate similar nucleic acid sequences from chromosomal DNA as described by Walsh PS et al (1992) PCR Methods Appl 1: 241–250.

Probes may be derived from naturally occurring or recombinant single- or double-stranded nucleic acids or be chemically synthesized. They may be labeled by nick translation, Klenow fill-in reaction, PCR or other methods well known in the art. Probes of the present invention, their preparation and/or labeling are elaborated in Sambrook J et al (1989) Molecular Cloning: A Laboratory Manual, 2 d Ed., Cold Spring Harbor; or Ausubel FM et al (1989) Current Protocols in Molecular Biology, Vol 2. John Wiley & Sons, both incorporated herein by reference.

Alternatively, recombinant variants encoding these same or similar polypeptides may be synthesized or selected by making use of the "redundancy" in the genetic code. Various codon substitutions, such as the silent changes which produce various restriction sites, may be introduced to optimize cloning into a plasmid or viral vector or expression in a particular prokaryotic or eukaryotic system. Mutations may also be introduced to modify the properties of the polypeptide, to change ligand-binding affinities, interchain affinities, or polypeptide degradation or turnover rate.

DETAILED DESCRIPTION OF THE INVENTION

The present invention provides a nucleotide sequence uniquely identifying novel chemokines of the C—C family, LVEC-1, LVEC-2, and PGEC, which are highly expressed in activated or inflamed tissues. Because each of these ECs is specifically expressed in the tissue from which it was identified and has not been found in other tissues, it is useful to have a diagnostic test for each particular EC. Excessive expression of the EC leads to attraction of neutrophils, monocytes/macrophages and/or T and B lymphocytes to the area and induces their production of excess proteases and other molecules which can lead to tissue damage or destruction. Therefore, a diagnostic test for excess expression of a particular EC can accelerate diagnosis and proper treatment of the inflammation before extensive tissue damage or destruction occurs.

Nucleotide sequences encoding ECs (or their complement) have numerous applications in techniques known to those skilled in the art of molecular biology. These techniques include use as hybridization probes, use for chromosome and gene mapping, use in the recombinant production of ECs, and use in generation of anti-sense RNA and DNA or their chemical analogs and the like. Uses of oligonucleotides encoding ECs disclosed herein are exemplary of known techniques and are not intended to limit their use in any technique known to a person of ordinary skill in the art. Furthermore, the nucleotide sequences disclosed herein may be used in molecular biology techniques that have not yet been developed, provided the new techniques rely on properties of polynucleotide sequences that are currently known, e.g., the triplet genetic code, specific base pair interactions, etc.

It will be appreciated by those skilled in the art that as a result of the degeneracy of the genetic code, a multitude of EC-encoding nucleotide sequences, some bearing minimal nucleotide sequence homology to the nucleotide sequence of any known and naturally occurring EC gene, may be produced. The invention has specifically contemplated each and every possible variation of nucleotide sequence that could be made by selecting combinations based on possible codon choices. These combinations are made in accordance with the standard triplet genetic code as applied to the nucleotide sequence of naturally occurring EC, and all such variations are to be considered as being specifically disclosed.

Although nucleotide sequences which encode ECs and/or EC variants are preferably capable of hybridizing to the nucleotide sequence of the naturally occurring EC gene under stringent conditions, it may be advantageous to produce nucleotide sequences encoding EC or EC derivatives possessing a substantially different codon usage. Codons can be selected to increase the rate at which expression of the peptide occurs in a particular prokaryotic or eukayotic expression host in accordance with the frequency with which a particular codon is utilized by the host. Other reasons for substantially altering the nucleotide sequence encoding ECs and/or EC derivatives without altering the encoded aa sequence include the production of RNA transcripts having more desirable properties, e.g., a greater half-life, than transcripts produced from the naturally occurring nucleotide sequence.

Nucleotide sequences encoding ECs may be joined to a variety of other nucleotide sequences by means of well established recombinant DNA techniques (cf Sambrook J et al. (1989) Molecular Cloning: A Laboratory Manual, 2 d Ed. Cold Spring Harbor).

Useful nucleotide sequences for joining to EC sequences include an assortment of cloning vectors, e.g., plasmids, cosmids, lambda phage derivatives, phagemids, and the like, that are known in the art. Vectors of interest include expression vectors, replication vectors, probe generation vectors, sequencing vectors, and the like. In general, vectors of interest may contain an origin of replication functional in at least one organism, convenient restriction endonuclease sensitive sites, and selectable markers for the host cell.

Another aspect of the subject invention is to provide for EC-specific nucleic acid hybridization probes capable of hybridizing with naturally occurring nucleotide sequences encoding ECs. Such probes for the detection of similar EC encoding sequences should preferably contain at least 50% of the nucleotides from a C—X—C or C—C encoding sequence. The hybridization probes of the subject invention may be derived from the nucleotide sequences of the SEQ ID NOs 1, 3, and 5, or from genomic sequences including promoters, enhancer elements and introns of naturally occuring ECs. Hybridization probes may be labeled by a variety of reporter groups, including radionuclides such as $^{32}P$ or $^{35}S$, or enzymatic labels such as alkaline phosphatase, coupled to the probe via avidin/biotin coupling systems, and the like.

PCR as described U.S. Pat. Nos. 4,965,188 and 4,683,195 and 4,800,195 provides additional uses for oligonucleotides based upon the nucleotide sequences which encode ECs. Such probes used in PCR may be of recombinant origin, may be chemically synthesized, or a mixture of both and comprise a discrete nucleotide sequence for diagnostic use or a degenerate pool of possible sequences for identification of closely related genomic sequences.

Other means of producing EC-specific hybridization probes include the cloning of nucleic acid sequences encoding ECs and EC derivatives into vectors for the production of mRNA probes. Such vectors are known in the art and are commercially available and may be used to synthesize RNA probes in vitro by means of the addition of the appropriate RNA polymerase as T7 or SP6 RNA polymerase and the appropriate radioactively labeled nucleotides.

It is now possible to produce a DNA sequence, or portions thereof, encoding EC and EC derivatives entirely by synthetic chemistry, after which the gene can be inserted into any of the many available DNA vectors using reagents, vectors and cells that are known in the art at the time of the filing of this application. Synthetic chemistry may be used to reproduce the entire sequence of a EC encoding gene, any portion thereof, or to introduce mutations into the sequence.

The nucleotide sequence for a particular EC can be used to construct an assay to detect inflammation and disease associated with abnormal levels of expression of that EC. The nucleotide sequence can be labeled by methods known in the art and added to a fluid or tissue sample from a patient under hybridizing conditions. After an incubation period, the sample is washed with compatible fluid which optionally contains a dye if the nucleotide has been labeled with an enzyme or other labeled requiring a developer. If the nucleotide sequence hybridizes with the sample, the dye is detected. The amount of dye detected is compared with a standard. If the amount of dye varies significantly from the standard, EC is present at an abnormal level and may indicate the presence of inflammation or disease.

The nucleotide sequence for an EC can be used to construct hybridization probes for mapping the gene which encodes that EC and for the genetic analysis of individuals with EC genetic disorders, allelic variants or other genetic traits of interest. The nucleotide sequences provided herein may be mapped to a chromosome and specific regions of a chromosomes using well known genetic and/or chromosomal mapping techniques. These techniques include in situ hybridization, linkage analysis against known chromosomal markers, hybridization screening with libraries or flow-sorted chromosomal preparations specific to known chromosomes, and the like. The technique of fluorescent in situ hybridization of chromosome spreads has been described, among other places, in Verma et al (1988) Human Chromosomes: A Manual of Basic Techniques, Pergamon Press, N.Y. Fluorescent in situ hybridization of chromosomal preparations and other physical chromosome mapping techniques may be correlated with additional genetic map data. Examples of genetic map data can be found in O'Brien (1990) Genetic Maps: Locus Maps of Complex Genomes, Book 5: Human Maps, Cold Spring Harbor Laboratory Press. Correlation between the location of a gene encoding an EC on a physical chromosomal map and a specific disease (or predisposition to a specific disease) can help detect genetic diseases and carrier states. The nucleotide sequence of the subject invention can be used to detect differences in gene sequence between normal and affected individuals.

Nucleotide sequences encoding ECs may be used to produce purified ECs using well known methods of recombinant DNA technology. Among the many publications that teach methods for the expression of genes after they have been isolated is Goeddel (1990) Gene Expression Technology, Methods and Enzymology. Vol 185, Academic Press, San Diego. EC may be expressed in a variety of host cells, either prokaryotic or eukaryotic. Host cells may be from species either the same or different than the species from which the nucleotide sequences encoding EC are endogenous. Advantages of producing the EC by recombinant DNA technology include obtaining highly enriched sources of the proteins for purification and the availability of simplified purification procedures.

Cells transformed with DNA encoding EC may be cultured under conditions suitable for the expression of the EC and the recovery of the protein from the cell culture. EC produced by a recombinant cell may be secreted or may be contained intracellularly, depending on the particular genetic construction used. In general, it is more convenient to prepare recombinant proteins in secreted form. Purification steps will depend on the nature of the production process used and the particular EC produced.

In addition to recombinant production, EC fragments may be produced by direct peptide synthesis using solid-phase techniques (cf Stewart et al (1969) Solid-Phase Peptide Synthesis, WH Freeman Co. San Francisco; Merrifield R (1963) J Am Chem Soc 85: 2149–2154. In vitro protein synthesis may be performed using manual techniques or by automation. Automated synthesis may be achieved, for example, using Applied Biosystems 431A Peptide Synthesizer (Foster City, Calif.) in accordance with the instructions provided by the manufacturer. Various fragments of ECs may be chemically synthesized separately and combined using chemical methods to produce full length ECs.

ECs for use in the induction of antibodies do not need to have biological activity; however, they must have immunogenic activity. Peptides for use in the induction of EC-specific antibodies may have an aa sequence consisting of at least five aa, preferably at least 10 aa. They should mimic a portion of the aa sequence of the particular EC and may contain the entire aa sequence of the naturally occurring EC. Short stretches of EC aa may be fused with those of another protein such as keyhole limpet hemocyanin and the chimeric molecule used for antibody production.

Antibodies specific for a particular EC may be produced by inoculation of an appropriate animal with the EC. An antibody is specific for an EC if the antibody is produced against all or part of the EC polypeptide and binds to all or part of the protein. Induction of antibodies includes not only the stimulation of an immune response by injection into animals, but also analogous steps in the production of synthetic antibodies or other specific-binding molecules such as the screening of recombinant immunoglobulin libraries (cf Orlandi et al (1989) PNAS 86: 3833–3837, or Huse et al (1989) Science 256: 1275–1281) or the in vitro stimulation of lymphocyte populations. Current technology (Winter and Milstein (1991) Nature 349: 293–299) provides for a number of highly specific binding reagents based on the principles of antibody formation. These techniques may readily be adapted to produce molecules capable of specifically binding ECs.

The examples below are provided to illustrate the subject invention. These examples are provided by way of illustration and are not included for the purpose of limiting the invention.

EXAMPLES

I Isolation of mRNA and construction of cDNA libraries

The cDNA sequences which encode LVEC-1 and LVEC-2 were identified among the sequences comprising the normal liver library. Poly A mRNA was isolated from the liver of a 49 year old, Caucasian male (Catalogue #937220; Stratagene, 11011 N. Torrey Pines Rd., La Jolla, Calif. 92037) and used to construct a custom cDNA library as described below.

The cDNA which encodes PGEC was also identified among the sequences comprising the pituitary gland library. Poly A mRNA was isolated from a pooled sample of 21 whole, normal pituitary glands from human brains of Caucasian males and females with a range of ages from 16–70 years. The poly A+ mRNA was obtained from Clontech Laboratories Inc. (Catalogue #6584-1 and #6584-2, 4030 Fabian Way, Palo Alto, Calif. 94303) and used to construct a cDNA library as described below.

The liver and pituitary gland cDNA libraries were constructed by Stratagene (11011 N. Torrey Pines Rd., La Jolla, Calif. 92037) using poly A mRNA. cDNA synthesis was primed using oligo dT and/or random hexamers. Synthetic adapter oligonucleotides were ligated onto cDNA ends enabling its insertion into the UNI-ZAP™ vector system (Stratagene). This allows high efficiency unidirectional (sense orientation) lambda library construction and the convenience of a plasmid system with blue/white color selection to detect clones with cDNA insertions.

The quality of the each cDNA library was screened using either DNA probes or antibody probes, and then the pBluescript® phagemid (Stratagene) was rapidly excised in living cells. The phagemid allows the use of a plasmid system for easy insert characterization, sequencing, site-directed mutagenesis, the creation of unidirectional deletions and expression of fusion proteins. Phage particles from each library were infected into the *E. coil* host strain XL1-BLUE® (Stratagene). The high transformation efficiency of XL1-BLUE® increases the probability of obtaining rare, under-represented clones from the cDNA library.

II Isolation of cDNA Clones

The phagemid forms of individual cDNA clones were obtained by the in vivo excision process, in which a host *E. coil* strain, (XL1-BLUE® MRF) was coinfected with an f1 helper phage. Proteins derived from both lambda phage and f1 helper phage initiate new DNA synthesis from defined sequences on the lambda target DNA and create a smaller, single stranded circular phagemid DNA molecule that includes all DNA sequences of the pBluescript® plasmid and the cDNA insert. The phagemid DNA is released from the cells and purified, then used to re-infect fresh bacterial host cells (SOLR), where the double stranded phagemid DNA was produced. Because the phagemid carries the gene for β-lactamase, the newly transformed bacteria are selected on medium containing ampicillin.

Phagemid DNA was purified using the QIAWELL-8 Plasmid Purification System or QIAGEN® DNA Purification System (QIAGEN Inc., 9259 Eton Ave., Chatsworth, Calif. 91311). This technique provides a rapid and reliable high-throughput method for lysing the bacterial cells and isolating highly purified phagemid DNA. The DNA eluted from the purification resin is suitable for DNA sequencing and other analytical manipulations.

III Sequencing of cDNA Clones

The cDNA inserts from random isolates of the liver and pituitary gland libraries were sequenced in part. Methods for DNA sequencing are well known in the art. Conventional enzymatic methods employ DNA polymerase Klenow fragment, SEQUENASE™ or Taq polymerase to extend DNA chains from an oligonucleotide primer annealed to the DNA template of interest. Methods have been developed for the use of both single- and double-stranded templates. The chain termination reaction products are usually electrophoresed on urea-acrylamide gels and are detected either by autoradiography (for radionuclide-labeled precursors) or by fluorescence (for fluorescent-labeled precursors). Recent improvements in mechanized reaction preparation, sequencing and analysis using the fluorescent detection method have permitted expansion in the number of sequences that can be determined per day (using machines such as the Catalyst 800 and the Applied Biosystems 373 DNA sequencer).

IV Homology Searching of cDNA Clones and Deduced Protein

Each sequence so obtained was compared to sequences in GenBank using a search algorithm developed by Applied Biosystems Inc. and incorporated into the INHERIT™ 670 Sequence Analysis System. In this algorithm, Pattern Specification Language (developed by TRW Inc.) was used to determine regions of homology. The three parameters that determine how the sequence comparisons run were window size, window offset, and error tolerance. Using a combination of these three parameters, the DNA database was searched for sequences containing regions of homology to the query sequence, and the appropriate sequences were scored with an initial value. Subsequently, these homologous regions were examined using dot matrix homology plots to distinguish regions of homology from chance matches. Smith-Waterman alignments were used to display the results of the homology search.

Peptide and protein sequence homologies can also be ascertained using the INHERIT 670 Sequence Analysis System in a way similar to that used in DNA sequence homologies. Pattern Specification Language and parameter windows were used to search protein databases for sequences containing regions of homology which were scored with an initial value. Dot-matrix homology plots were examined to distinguish regions of significant homology from chance matches.

V Identification and Full Length Sequencing of EC

From all of the randomly picked and sequenced clones of the liver library, two sequences were homologous to but clearly different from one another and from known C—C chemokine molecules. These sequences were found within Incyte clones 87825 and 88564 and have been designated Ivec-1 and Ivec-2, respectively. When all three possible predicted translations of the sequence were searched against protein databases such as SwissProt and PIR, no exact matches were found to either of the expressed proteins, LVEC-1 and LVEC-2.

From all of the randomly picked and sequenced clones of the pituitary gland library, only one sequence was homologous to but clearly different from known C—C chemokine molecules. This sequence was found within Incyte clone 111571 and has been designated pgec. When all three possible predicted translations of the sequence were searched against protein databases such as SwissProt and PIR, no exact matches were found to the expressed protein, PGEC.

VI Antisense analysis

Knowledge of the correct, complete cDNA sequences of the novel expressed chemokine genes will enable their use in antisense technology in the investigation of gene function. Either oligonucleotides, genomic or cDNA fragments comprising the antisense strand of Ivec-1, Ivec-2 or pgec can be used either in vitro or in vivo to inhibit expression of the specific protein. Such technology is now well known in the art, and probes can be designed at various locations along the nucleotide sequence. By treatment of cells or whole test animals with such antisense sequences, the gene of interest can be effectively turned off. Frequently, the function of the gene can be ascertained by observing behavior at the cellular, tissue or organismal level (e.g. lethality, loss of differentiated function, changes in morphology or the like).

In addition to using sequences constructed to the gene itself, modifications of gene expression can be obtained by designing antisense sequences to intron regions, promoter/enhancer elements, or even to trans-acting regulatory genes. Similarly, inhibition can be achieved using Hogeboom base-pairing methodology, also known as "triple helix" base pairing.

VII Expression of EC

Translation of any of the cloned chemokine cDNAs (Ivec-1, Ivec-2 or pgec) into protein may be accomplished by subcloning the cDNA into an appropriate expression vector and transfecting this vector into an appropriate expression host. In this particular case, the cloning vector used for the generation of the tissue library also provides for direct expression of the included sequence in *E. coli*. Upstream of the cloning site, this vector contains a promoter for β-galactosidase, followed by sequence containing the amino-terminal Met and the subsequent 7 residues of β-galactosidase. Immediately following these eight residues is an engineered bacteriophage promoter useful for artificial priming and transcription and a number of unique restriction sites (including Eco RI) for cloning.

Induction of the isolated bacterial strain with IPTG using standard methods will produce a fusion protein corresponding to the first seven residues of β-galactosidase, about 15 residues of "linker", and the peptide encoded within the cDNA. Since cDNA clone inserts are generated by an essentially random process, there is one chance in three that the included cDNA will lie in the correct frame for proper translation. If the cDNA is not in the proper reading frame, it can be obtained by deletion or insertion of the appropriate number of bases by well known methods including in vitro mutagenesis, digestion with exonuclease III or mung bean nuclease, or oligonucleotide linker inclusion. The EC molecule of interest will be expressed in the bacterial system as described.

Any particular chemokine cDNA sequence can be shuttled to other vectors known to be useful for expression of protein in specific hosts. Oligonucleotide amplimers containing cloning sites as well as a segment of DNA sufficient to hybridize to stretches at both ends of the target cDNA (25 bases) can be synthesized chemically by standard methods. These primers can then used to amplify the desired gene segments by PCR. The resulting new gene segments can be digested with appropriate restriction enzymes under standard conditions and isolated by gel electrophoresis. Alternately, similar gene segments can be produced by digestion of the cDNA with appropriate restriction enzymes and filling in the missing gene segments with chemically synthesized oligonucleotides. Segments of the coding sequence from more than one gene can be ligated together and cloned in appropriate vectors to optimize expression of recombinant sequence.

Suitable expression hosts for such chimeric molecules include but are not limited to mammalian cells such as Chinese Hamster Ovary and human 293 cells, insect cells such as Sf9 cells, yeast cells such as *Saccharomyces cerevisiae*, and bacteria such as *E. coli*. For each of these cell systems, a useful expression vector may also include an origin of replication to allow propagation in bacteria and a selectable marker such as the β-lactamase antibiotic resistance gene to allow selection in bacteria. In addition, the vectors may include a second selectable marker such as the neomycin phosphotransferase gene to allow selection in transfected eukaryotic host cells. Vectors for use in eukaryotic expression hosts may require RNA processing elements such as 3' polyadenylation sequences if such are not part of the cDNA of interest.

Additionally, the vector may contain promoters or enhancers which increase gene expression. Such promoters are host specific and include MMTV, SV40, or metallothionine promoters for CHO cells; trp, lac, tac or T7 promoters for bacterial hosts, or alpha factor, alcohol oxidase or PGH promoters for yeast. Transcription enhancers, such as the RSV enhancer, may be used in mammalian host cells. Once homogeneous cultures of recombinant cells are obtained through standard culture methods, large quantities of recombinantly produced ECs can be recovered from the conditioned medium and analyzed using chromatographic methods known in the art.

VIII Isolation of Recombinant EC

ECs may be expressed as a chimeric protein with one or more additional polypeptide domains added to facilitate protein purification. Such purification facilitating domains include, but are not limited to, metal chelating peptides such as histidine-tryptophan modules that allow purification on immobilized metals, protein A domains that allow purification on immobilized immunoglobulin, and the domain utilized in the FLAGS extension/affinity purification system (Immunex Corp., Seattle Wash.). The inclusion of a cleavable linker sequence (such as Factor XA or enterokinase) between the purification domain and the EC-encoding sequence may be useful to facilitate production of EC.

IX Production of EC-Specific Antibodies

Two approaches are utilized to raise antibodies to ECs, and each approach is useful for generating either polyclonal or monoclonal antibodies. In one approach, denatured EC from the reverse phase HPLC separation is obtained in quantities up to 75 mg. This denatured protein can be used to immunize mice or rabbits using standard protocols; about 100 micrograms are adequate for immunization of a mouse, while up to 1 mg might be used to immunize rabbit. For identifying mouse hybridomas, the denatured protein can be radioiodinated and used to screen potential murine B-cell hybridomas for those which produce antibody. This procedure requires only small quantities of protein, such that 20 mg would be sufficient for labeling and screening of several thousand clones.

In the second approach, the amino acid sequence of EC, as deduced from the cDNA, is analyzed to determine regions of high immunogenicity. Polypeptides comprising these regions are synthesized and used in suitable immunization protocols to raise antibodies. Analysis to select appropriate epitopes is described by Ausubel FM et al (1989, Current Protocols in Molecular Biology, Vol 2. John Wiley & Sons). The optimal amino acid sequences for immunization are usually at the C-terminus, the N-terminus and those intervening, hydrophilic regions of the polypeptide which are likely to be exposed to the external environment when the protein is in its natural conformation.

Typically, selected peptides, about 15 residues in length, are synthesized using an Applied Biosystems Peptide Synthesizer Model 431A using fmoc-chemistry and coupled to keyhole limpet hemocyanin (KLH, Sigma) by reaction with M- maleimidobenzoyl-N-hydroxysuccinimide ester (MBS; cf. Ausubel FM et al, supra). If necessary, a cysteine may be introduced at the N-terminus of the peptide to permit coupling to KLH. Rabbits are immunized with the peptide-KLH complex in complete Freund's adjuvant. The resulting antisera are tested for antipeptide activity by binding the peptide to plastic, blocking with 1% BSA, reacting with antisera, washing and reacting with labeled (radioactive or fluorescent), affinity purified, specific goat anti-rabbit IgG.

Hybridomas may also be prepared and screened using standard techniques. Hybridomas of interest are detected by screening with labeled EC to identify those fusions producing the monoclonal antibody with the desired specificity. In a typical protocol, wells of plates (FAST, Becton-Dickinson, Palo Alto, Calif.) are coated with affinity purified, specific rabbit-anti-mouse (or suitable anti-species Ig) antibodies at 10 mg/ml. The coated wells are blocked with 1% BSA, washed and exposed to supernatants from hybridomas. After incubation the wells are exposed to labeled EC, 1 mg/ml. Clones producing antibodies will bind a quantity of labeled EC which is detectable above background. Such clones are expanded and subjected to 2 cycles of cloning at limiting dilution (1 cell/3 wells). Cloned hybridomas are injected into pristine mice to produce ascites, and monoclonal antibody is purified from mouse ascitic fluid by affinity chromatography on Protein A. Monoclonal antibodies with affinities of at least $10^8$ $M^{-1}$, preferably $10^9$ to $10^{10}$ or stronger, will typically be made by standard procedures as described in Harlow and Lane (1988) Antibodies: A Laboratory Manual. Cold Spring Harbor Laboratory, or Goding (1986) Monoclonal Antibodies: Principles and Practice, 2 Ed. Academic Press N.Y., both incorporated herein by reference.

X Diagnostic Test Using EC-Specific Antibodies

Particular EC antibodies are useful for the diagnosis of prepathologic conditions, and chronic or acute diseases which are characterized by differences in the amount or distribution of that EC. To date, each EC has only been found in that particular tissue from which it was cloned and is thus specific for abnormalities or pathologies of that tissue.

Diagnostic tests for EC include methods utilizing the antibody and a label to detect EC in human body fluids, tissues or extracts of such tissues. The polypeptides and antibodies of the present invention may be used with or without modification. Frequently, the polypeptides and antibodies will be labeled by joining them, either covalently or noncovalently, with a substance which provides for a detectable signal. A wide variety of labels and conjugation techniques are known and have been reported extensively in both the scientific and patent literature. Suitable labels include radionuclides, enzymes, substrates, cofactors, inhibitors, fluorescent agents, chemiluminescent agents, magnetic particles and the like. Patents teaching the use of such labels include U.S. Pat. Nos. 3,817,837; 3,850,752; 3,939,350; 3,996,345; 4,277,437; 4,275,149; and 4,366,241. Also, recombinant immunoglobulins may be produced as shown in U.S. Pat. No. 4,816,567, incorporated herein by reference.

A variety of protocols for measuring soluble or membrane-bound EC, using either polyclonal or monoclonal antibodies specific for that EC are known in the art. Examples include enzyme-linked immunosorbent assay (ELISA), radioimmunoassay (RIA) and fluorescent activated cell sorting (FACS). A two-site monoclonal-based immunoassay utilizing monoclonal antibodies reactive to two non-interfering epitopes on EC is preferred, but a competitive binding assay may be employed. These assays are described, among other places, in Maddox, Del. et al (1983) J Exp Med 158: 1211.

XI Purification of Native EC Using Specific Antibodies

Native or recombinant ECs may be purified by immunoaffinity chromatography using EC-specific antibodies. In general, an immunoaffinity column is constructed by covalently coupling the anti-EC antibody to an activated chromatographic resin.

Polyclonal immunoglobulins are prepared from immune sera either by precipitation with ammonium sulfate or by purification on immobilized Protein A (Pharmacia LKB Biotechnology, Piscataway, N.J.). Likewise, monoclonal antibodies are prepared from mouse ascites fluid by ammonium sulfate precipitation or chromatography on immobilized Protein A. Partially purified Ig is covalently attached to a chromatographic resin such as CnBr activated Sepharose (Pharmacia LKB Biotechnology, Piscataway, N.J.). The antibody is coupled to the resin, the resin is blocked, and the derivative resin is washed according to the manufacturer's instructions.

Such an immunoaffinity column is utilized in the purification of EC by preparing a fraction from cells containing EC in a soluble form. This preparation may be derived by solubilization of the whole cell or of a subcellular fraction obtained via differential centrifugation by the addition of detergent or by other methods well known in the art. Alternatively, soluble EC containing a signal sequence may be secreted in useful quantity into the medium in which the cells are grown.

A soluble EC-containing preparation is passed over the immunoaffinity column, and the column is washed under conditions, e.g., high ionic strength buffers in the presence of detergent, that allow the preferential absorbance of EC. Then, the column is eluted under conditions that disrupt antibody/EC binding (e.g., a buffer of pH 2–3 or a high concentration of a chaotrope such as urea or thiocyanate ion), and the EC is collected.

XII Determination of EC-Induced Chemotaxis or Cell Activation

The chemotactic activity of EC is measured in a 48-well microchemotaxis chamber (Falk WR et al (1980) J Immunol Methods 33: 239). In each well, two compartments are separated by a filter that allows the passage of cells in response to a chemical gradient. Cell culture medium such as RMPI 1640 containing EC is placed on one side of a filter, usually polycarbonate, and cells suspended in the same media are placed on the opposite side of the filter. Sufficient incubation time is allowed for the cells to traverse the filter in response to the concentration gradient across the filter. Filters are recovered from each well, and cells adhering to the side of the filter facing EC are typed and quantified.

The specificity of the chemoattraction is determined by performing the chemotaxis assay on specific populations of cells. First, blood cells obtained from venipuncture are fractionated by density gradient centrifugation and the chemotactic activity of the particular EC is tested on enriched populations of neutrophils, peripheral blood mononuclear cells, monocytes and lymphocytes. Optionally, such enriched cell populations are further fractionated using $CD8^+$ and $CD4^+$ specific antibodies for negative selection of $CD4^+$ and $CD8^+$ enriched T-cell populations, respectively.

Another assay elucidates the chemotactic effect of EC on activated T-cells. There, unfractionated T-cells or fractionated T-cell subsets are cultured for 6 to 8 hours in tissue culture vessels coated with CD-3 antibody. After this CD-3 activation, the chemotactic activity of EC is tested as described above. Many other methods for obtaining enriched cell populations are known in the art.

Some chemokines also produce a non-chemotactic cell activation of neutrophils and monocytes. This is tested via standard measures of neutrophil activation such as actin polymerization, increase in respiratory burst activity, degranulation of the azurophilic granule and mobilization of $Ca^{++}$ as part of the signal transduction pathway. The assay for mobilization of $Ca^{++}$ involves preloading neutrophils with a fluorescent probe whose emission characteristics have been altered by $Ca^{++}$ binding. When the cells are exposed to an activating stimulus, $Ca^{++}$ flux is determined by observation of the cells in a fluorometer. The measurement of $Ca^{++}$ mobilization has been described in Grynkievicz G et al. (1985) J Biol Chem 260: 3440, and McColl S et al. (1993) J Immunol 150: 4550–4555, incorporated herein by reference.

Degranulation and respiratory burst responses are also measured in monocytes (Zachariae COC et al. (1990) J Exp Med 171: 2177–82). Further measures of monocyte activation are regulation of adhesion molecule expression and cytokine production (Jiang Y et al. (1992) J Immunol 148: 2423–8). Expression of adhesion molecules also varies with lymphocyte activation (Taub D et al. (1993) Science 260: 355–358).

XIII Drug Screening

This invention is particularly useful for screening compounds by using the EC polypeptide or binding fragment thereof in any of a variety of drug screening techniques. The EC polypeptide or fragment employed in such a test may either be free in solution, affixed to a solid support, borne on a cell surface or located intracellularly. One method of drug screening utilizes eucaryotic or procaryotic host cells which are stably transformed with recombinant nucleic acids expressing the polypeptide or fragment. Drugs are screened agsinst such transformed cells in competitive binding assays. Such cells, either in viable or fixed form, can be used for standard binding assays. One may measure, for example, the formation of complexes between an EC polypeptide or fragment and the agent being tested or examine the diminution in complex formation between a EC polypeptide or fragment and cell caused by the agent being tested.

Thus, the present invention provides methods of screening for drugs or any other immunomodulating agents which can affect inflammation and disease. These methods comprise contacting such an agent with a EC polypeptide or fragment thereof and assaying (i) for the presence of a complex between the agent and the EC polypeptide or fragment, or (ii) for the presence of a complex between the EC polypeptide or fragment and the cell, by methods well known in the art. In such competitive binding assays, the EC polypeptide or fragment is typically labeled. After suitable incubation, free EC polypeptide or fragment is separated from that present in bound form, and the amount of free or uncomplexed label is a measure of the ability of the particular agent to bind to EC or to interfere with the EC/cell complex.

Another technique for drug screening provides high throughput screening for compounds having suitable binding affinity to the EC polypeptides and is described in detail in Geysen, European Patent Application 84/03564, published on Sep. 13, 1984, incorporated herein by reference. Briefly stated, large numbers of different small peptide test compounds are synthesized on a solid substrate, such as plastic pins or some other surface. The peptide test compounds are reacted with EC polypeptide and washed. Bound EC polypeptide is then detected by methods well known in the art. Purified EC can also be coated directly onto plates for use in the aforementioned drug screening techniques. In addition, non-neutralizing antibodies can be used to capture the peptide and immobilize it on the solid support.

This invention also contemplates the use of competitive drug screening assays in which neutralizing antibodies capable of binding EC specifically compete with a test compound for binding to EC polypeptide or fragments thereof. In this manner, the antibodies can be used to detect the presence of any peptide which shares one or more antigenic determinants with EC.

XIV Rational Drug Design

The goal of rational drug design is to produce structural analogs of biologically active polypeptides of interest or of small molecules with which they interact, e.g., agonists, antagonists, or inhibitors. Any of these examples can be used to fashion drugs which are more active or stable forms of the polypeptide or which enhance or interfere with the function of a polypeptide in vivo (cf. Hodgson J (1991) Bio/Technology 9: 19–21, incorporated herein by reference).

In one approach, the three-dimensional structure of a protein of interest, or of a protein-inhibitor complex, is determined by x-ray crystallography, by computer modeling or, most typically, by a combination of the two approaches. Both the shape and charges of the polypeptide must be ascertained to elucidate the structure and to determine active site(s) of the molecule. Less often, useful information regarding the structure of a polypeptide may be gained by modeling based on the structure of homologous proteins. In both cases, relevant structural information is used to design analogous chemokine-like molecules or to identify efficient inhibitors. Useful examples of rational drug design may include molecules which have improved EC activity or stability as shown by Braxton S and Wells JA (1992 Biochemistry 31: 7796–7801) or which act as inhibitors, agonists, or antagonists of native EC as shown by Athauda SB et al (1993 J Biochem 113: 742–746), incorporated herein by reference.

It is also possible to isolate a target-specific antibody, selected by functional assay, as described above, and then to solve its crystal structure. This approach, in principle, yields a pharmacore upon which subsequent drug design can be based. It is possible to bypass protein crystallography altogether by generating anti-idiotypic antibodies (anti-ids) to a functional, pharmacologically active antibody. As a mirror image of a mirror image, the binding site of the anti-ids would be expected to be an analog of the original receptor. The anti-id could then be used to identify and isolate peptides from banks of chemically or biologically produced peptides. The isolated peptides would then act as the pharmacore.

By virtue of the present invention, sufficient amount of polypeptide may be made available to perform such analytical studies as X-ray crystallography. In addition, knowledge of the EC amino acid sequence provided herein will provide guidance to those employing computer modeling techniques in place of or in addition to x-ray crystallography.

XV Identification of EC Receptors

Purified EC is useful for characterization and purification of specific cell surface receptors and other binding molecules. Cells which respond to a particular EC by chemotaxis or other specific responses are likely to express a receptor for that EC. Radioactive labels may be incorporated into EC by various methods known in the art. A preferred embodiment is the labeling of primary amino groups in EC with $^{125}$I Bolton-Hunter reagent (Bolton, AE and Hunter, WM (1973) Biochem J 133: 529), which has been used to label other chemokines without concomitant loss of biological activity (Hebert CA et al (1991) J Biol Chem 266: 18989; McColl S et al (1993) J Immunol 150: 4550–4555). Receptor-bearing cells are incubated with labeled EC. The cells are then washed to removed unbound EC, and receptor-bound EC is quantified. The data obtained using different concentrations of EC are used to calculate values for the number and affinity of receptors.

Labeled EC is useful as a reagent for purification of its specific receptor. In one embodiment of affinity purification, the EC is covalently coupled to a chromatography column. Receptor-bearing cells are extracted, and the extract is passed over the column. The receptor binds to the column by virtue of its biological affinity for its receptor. The receptor is recovered from the column and subjected to N-terminal protein sequencing. This amino acid sequence is then used to design degenerate oligonucleotide probes for cloning the receptor.

In an alternate method, expression cloning, mRNA is obtained from receptor-bearing cells and made into a cDNA expression library. The library is transfected into a population of cells, and those cells in the population which express the receptor are selected using fluorescently labeled EC. The receptor is identified by recovering and sequencing recombinant DNA from highly labeled cells.

In another alternate method, antibodies are raised against the surface of receptor-bearing cells, specifically monoclonal antibodies. The monoclonal antibodies are screened to identify those which inhibit the binding of labeled EC. These monoclonal antibodies are then used in affinity purification or expression cloning of the receptor.

Soluble receptors or other soluble binding molecules are identified in a similar manner. Labeled ECs are incubated with extracts or other appropriate materials derived from their specific inflamed or diseased tissue. After incubation, EC complexes larger than the size of purified EC are identified by a sizing technique such as size exclusion chromatography or density gradient centrifugation and are purified by methods known in the art. The soluble receptors or binding protein(s) are subjected to N-terminal sequencing to obtain information sufficient for database identification, if the soluble protein is known, or cloning, if the soluble protein is unknown.

XVI Use and Administration of ECs

Antibodies, inhibitors, receptors or analogs of the various ECs (treatments for excessive EC production, hereafter abbreviated TEC), can provide different effects when administered therapeutically. The TECs will be formulated in a nontoxic, inert, pharmaceutically acceptable aqueous carrier medium preferably at a pH of about 5 to 8, more preferably 6 to 8, although the pH may vary according to the characteristics of the antibody, inhibitor, receptor or analog being formulated and the condition to be treated. Characteristics of the TEC include solubility of the molecule, half-life and antigenicity/immunogenicity and may aid in defining an effective carrier. Native human proteins are preferred as TECs, but organic molecules resulting from drug screens may be equally effective in particular situations.

TECs may be delivered by known routes of administration including but not limited to topical creams or gels; transmucosal spray or aerosal, transdermal patch or bandage; injectable, intravenous or lavage formulations; or orally administered liquids or pills. The particular formulation, exact dosage, and route of administration will be determined by the attending physician and will vary according to each specific situation.

Such determinations are made by considering multiple variables such as the condition to be treated, the TEC to be administered, and the pharmacokinetic profile of the particular TEC. Additional factors which may be taken into account include disease state (e.g. severity) of the patient, age, weight, gender, diet, time of administration, drug combination, reaction sensitivities, and tolerance/response to therapy. Long acting TEC formulations might be administered every 3 to 4 days, every week, or once every two weeks depending on half-life and clearance rate of the particular TEC.

Normal dosage amounts may vary from 0.1 to 100,000-micrograms, up to a total dose of about 1 g, depending upon the route of administration. Guidance as to particular dosages for the TECs is provided in the literature; see U.S. Pat. Nos. 4,657,760; 5,206,344; or 5,225,212. It is anticipated that different formulations will be effective for different TECs and that administration targeting the liver may necessitate delivery in a manner different from that for delivery targeted to the pituitary gland.

It is contemplated that a liver condition or disease which activates leukocytes, particularly monocytes and macrophages, and precipitates permanent damage may be treatable with TECs. These conditions or diseases may be specifically diagnosed by the diagnostic tests discussed above, sucg testing should be performed in patients with fatty liver, jaundice, hepatitis, cirrhosis, amyloidosis, and cancer. Similarly treatable conditions or diseases of the pituitary can be diagnosed by specific testing, which should be performed for patients with adenoma or multiple endocrine neoplasia, as well as other genetic or invasive conditions that activate cells which may destroy or compromise the function of the pituitary gland.

All publications and patents mentioned in the above specification are herein incorporated by reference. The foregoing written specification is considered to be sufficient to enable one skilled in the art to practice the invention. Indeed, various modifications of the above described modes for carrying out the invention which are obvious to those skilled in the field of molecular biology or related fields are intended to be within the scope of the following claims.

SEQUENCE LISTING ( 1 ) GENERAL INFORMATION:

( i i i ) NUMBER OF SEQUENCES: 12

( 2 ) INFORMATION FOR SEQ ID NO:1:

( i ) SEQUENCE CHARACTERISTICS:
        ( A ) LENGTH: 363 base pairs
        ( B ) TYPE: nucleic acid
        ( C ) STRANDEDNESS: single
        ( D ) TOPOLOGY: linear ( i i ) MOLECULE TYPE: cDNA ( v i i ) IMMEDIATE SOURCE:
        ( A ) LIBRARY: LIVER
        ( B ) CLONE: 87825

( x i ) SEQUENCE DESCRIPTION: SEQ ID NO:1:

```
ATGAAGGTCT CCGAGGCTGC CCTGTCTCTC CTTGTCCTCA TCCTTATCAT TACTTCGGCT      60
TCTCGCAGCC AGCCAAAAGT TCCTGAGTGG GTGAACACCC CATCCACCTG CTGCCTGAAG     120
TATTATGAGA AAGTGTTGCC AAGGAGACTA GTGGTGGGAT ACAGAAAGGC CCTCAACTGT     180
CACCTGCCAG CAATCATCTT CGTCACCAAG AGGAACGAG  AAGTCTGCAC CAACCCCAAT     240
GACGACTGGG TCCAAGAGTA CATCAAGGAT CCCAACCTAC CTTTGCTGCC TACCAGGAAC     300
TTGTCCACGG TTAAAATTAT TACAGCAAAG AATGGTCAAC CCCAGCTCCT CAACTCCCAG     360
TGA                                                                   363
```

( 2 ) INFORMATION FOR SEQ ID NO:2:

( i ) SEQUENCE CHARACTERISTICS:
        ( A ) LENGTH: 120 amino acids
        ( B ) TYPE: amino acid
        ( C ) STRANDEDNESS: single
        ( D ) TOPOLOGY: linear ( i i ) MOLECULE TYPE: peptide ( v i i ) IMMEDIATE SOURCE:
        ( A ) LIBRARY: LIVER
        ( B ) CLONE: 87825

( x i ) SEQUENCE DESCRIPTION: SEQ ID NO:2:

```
Met Lys Val Ser Glu Ala Ala Leu Ser Leu Leu Val Leu Ile Leu Ile
 1               5                  10                  15
Ile Thr Ser Ala Ser Arg Ser Gln Pro Lys Val Pro Glu Trp Val Asn
             20                  25                  30
Thr Pro Ser Thr Cys Cys Leu Lys Tyr Tyr Glu Lys Val Leu Pro Arg
             35                  40                  45
Arg Leu Val Val Gly Tyr Arg Lys Ala Leu Asn Cys His Leu Pro Ala
         50                  55                  60
Ile Ile Phe Val Thr Lys Arg Asn Arg Glu Val Cys Thr Asn Pro Asn
65                  70                  75                  80
Asp Asp Trp Val Gln Glu Tyr Ile Lys Asp Pro Asn Leu Pro Leu Leu
                 85                  90                  95
Pro Thr Arg Asn Leu Ser Thr Val Lys Ile Ile Thr Ala Lys Asn Gly
            100                 105                 110
Gln Pro Gln Leu Leu Asn Ser Gln
            115                 120
```

( 2 ) INFORMATION FOR SEQ ID NO:3:

( i ) SEQUENCE CHARACTERISTICS:
    ( A ) LENGTH: 291 base pairs
    ( B ) TYPE: nucleic acid
    ( C ) STRANDEDNESS: single
    ( D ) TOPOLOGY: linear ( i i ) MOLECULE TYPE: cDNA ( v i i ) IMMEDIATE SOURCE:
    ( A ) LIBRARY: LIVER
    ( B ) CLONE: 88564

( x i ) SEQUENCE DESCRIPTION: SEQ ID NO:3:

| | | | | | |
|---|---|---|---|---|---|
| ATGTGCTGTA | CCAAGAGTTT | GCTCCTGGCT | GCTTTGATGT | CAGTGCTGCT | ACTCCACCTC | 60 |
| TGCGGCGAAT | CAGAAGCAGC | AAGCAACTTT | GACTGCTGTC | TTGGATACAC | AGACCGTATT | 120 |
| CTTCATCCTA | AATTTATTGT | GGGCTTCACA | CGGCAGCTGG | CCAATGAAGG | CTGTGACATC | 180 |
| AATGCTATCA | TCTTTCACAC | AAAGAAAAAG | TTGTCTGTGT | GCGCAAATCC | AAAACAGACT | 240 |
| TGGGTGAAAT | ATATTGTGCG | TCTCCTCAGT | AAAAAAGTCA | AGAACATGTA | A | 291 |

( 2 ) INFORMATION FOR SEQ ID NO:4:

( i ) SEQUENCE CHARACTERISTICS:
    ( A ) LENGTH: 96 amino acids
    ( B ) TYPE: amino acid
    ( C ) STRANDEDNESS: single
    ( D ) TOPOLOGY: linear ( i i ) MOLECULE TYPE: peptide ( v i i ) IMMEDIATE SOURCE:
    ( A ) LIBRARY: LIVER
    ( B ) CLONE: 88564

( x i ) SEQUENCE DESCRIPTION: SEQ ID NO:4:

Met Cys Cys Thr Lys Ser Leu Leu Leu Ala Ala Leu Met Ser Val Leu
 1               5                  10                 15

Leu Leu His Leu Cys Gly Glu Ser Glu Ala Ala Ser Asn Phe Asp Cys
             20                  25                 30

Cys Leu Gly Tyr Thr Asp Arg Ile Leu His Pro Lys Phe Ile Val Gly
         35                  40                 45

Phe Thr Arg Gln Leu Ala Asn Glu Gly Cys Asp Ile Asn Ala Ile Ile
     50                  55                 60

Phe His Thr Lys Lys Lys Leu Ser Val Cys Ala Asn Pro Lys Gln Thr
65                  70                 75                  80

Trp Val Lys Tyr Ile Val Arg Leu Leu Ser Lys Lys Val Lys Asn Met
                 85                 90                 95

( 2 ) INFORMATION FOR SEQ ID NO:5:

( i ) SEQUENCE CHARACTERISTICS:
    ( A ) LENGTH: 282 base pairs
    ( B ) TYPE: nucleic acid
    ( C ) STRANDEDNESS: single
    ( D ) TOPOLOGY: linear ( i i ) MOLECULE TYPE: cDNA ( v i i ) IMMEDIATE SOURCE:
    ( A ) LIBRARY: PITUITARY
    ( B ) CLONE: 115571

( x i ) SEQUENCE DESCRIPTION: SEQ ID NO:5:

ATGAAGATCT CCGTGGCTGC CATTCCCTTC TTCCTCCTCA TCACCATCGC CCTAGGGACC  60

```
AAGACTGAAT CCTCCTCACG GGGACCTTAC CACCCCTCAG AGTGCTGCTT CACCTACACT      120

ACCTACAAGA TCCCGCGTCA GCGGATTATG GATTACTATG AGACCAACAG CCAGTGCTCC      180

AAGCCCGGAA TTGTCTTCAT CACCAAAAGG GGCCATTCCG TCTGTACCAA CCCCAGTGAC      240

AAGTGGGTCC AGGACTATAT CAAGGACATG AAGGAGAACT GA                         282
```

( 2 ) INFORMATION FOR SEQ ID NO:6:

( i ) SEQUENCE CHARACTERISTICS:
        ( A ) LENGTH: 93 amino acids
        ( B ) TYPE: amino acid
        ( C ) STRANDEDNESS: single
        ( D ) TOPOLOGY: linear ( i i ) MOLECULE TYPE: peptide ( v i i ) IMMEDIATE SOURCE:
        ( A ) LIBRARY: PITUITARY
        ( B ) CLONE: 115571

( x i ) SEQUENCE DESCRIPTION: SEQ ID NO:6:

```
Met Lys Ile Ser Val Ala Ala Ile Pro Phe Phe Leu Leu Ile Thr Ile
 1               5                  10                  15

Ala Leu Gly Thr Lys Thr Glu Ser Ser Ser Arg Gly Pro Tyr His Pro
            20                  25                  30

Ser Glu Cys Cys Phe Thr Tyr Thr Thr Tyr Lys Ile Pro Arg Gln Arg
        35                  40                  45

Ile Met Asp Tyr Tyr Glu Thr Asn Ser Gln Cys Ser Lys Pro Gly Ile
    50                  55                  60

Val Phe Ile Thr Lys Arg Gly His Ser Val Cys Thr Asn Pro Ser Asp
65                  70                  75                  80

Lys Trp Val Gln Asp Tyr Ile Lys Asp Met Lys Glu Asn
                    85                  90
```

( 2 ) INFORMATION FOR SEQ ID NO:7:

( i ) SEQUENCE CHARACTERISTICS:
        ( A ) LENGTH: 92 amino acids
        ( B ) TYPE: amino acid
        ( C ) STRANDEDNESS: single
        ( D ) TOPOLOGY: linear ( i i ) MOLECULE TYPE: peptide ( v i i ) IMMEDIATE SOURCE:
        ( A ) LIBRARY: GENBANK
        ( B ) CLONE: GI 339728

( x i ) SEQUENCE DESCRIPTION: SEQ ID NO:7:

```
Met Lys Pro Thr Ala Met Ala Leu Met Cys Leu Leu Leu Ala Ala Val
 1               5                  10                  15

Trp Ile Gln Asp Val Asp Ser Lys Ser Met Leu Thr Val Ser Asn Ser
            20                  25                  30

Cys Cys Leu Asn Thr Leu Lys Lys Glu Leu Pro Leu Lys Phe Ile Gln
        35                  40                  45

Cys Tyr Arg Lys Met Gly Ser Ser Cys Pro Asp Pro Ala Val Val
    50                  55                  60

Phe Arg Leu Asn Lys Gly Arg Glu Ser Cys Ala Ser Thr Asn Lys Thr
65                  70                  75                  80

Trp Val Gln Asn His Leu Lys Lys Val Asn Pro Cys
                85                  90
```

( 2 ) INFORMATION FOR SEQ ID NO:8:

( i ) SEQUENCE CHARACTERISTICS:
  ( A ) LENGTH: 99 amino acids
  ( B ) TYPE: amino acid
  ( C ) STRANDEDNESS: single
  ( D ) TOPOLOGY: linear ( i i ) MOLECULE TYPE: peptide ( v i i ) IMMEDIATE SOURCE:
  ( A ) LIBRARY: GENBANK
  ( B ) CLONE: GI 487124

( x i ) SEQUENCE DESCRIPTION: SEQ ID NO:8:

```
Met Lys Val Ser Ala Ala Leu Leu Cys Leu Leu Leu Ile Ala Ala Thr
 1               5                  10                  15
Phe Ile Pro Gln Gly Leu Ala Gln Pro Asp Ala Ile Asn Ala Pro Val
                20                  25                  30
Thr Cys Cys Tyr Asn Phe Thr Asn Arg Lys Ile Ser Val Gln Arg Leu
                35                  40                  45
Ala Ser Tyr Arg Arg Ile Thr Ser Ser Lys Cys Pro Lys Glu Ala Val
        50                  55                  60
Ile Phe Lys Thr Ile Val Ala Lys Glu Ile Cys Ala Asp Pro Lys Gln
65                  70                  75                  80
Lys Trp Val Gln Asp Ser Met Asp His Leu Asp Lys Gln Thr Gln Thr
                85                  90                  95
Pro Lys Thr
```

( 2 ) INFORMATION FOR SEQ ID NO:9:

( i ) SEQUENCE CHARACTERISTICS:
    ( A ) LENGTH: 77 amino acids
    ( B ) TYPE: amino acid
    ( C ) STRANDEDNESS: single
    ( D ) TOPOLOGY: linear ( i i ) MOLECULE TYPE: peptide ( v i i ) IMMEDIATE SOURCE:
    ( A ) LIBRARY: GENBANK
    ( B ) CLONE: GI 126829

( x i ) SEQUENCE DESCRIPTION: SEQ ID NO:9:

```
Ala Gln Pro Asp Ser Val Ser Ile Pro Ile Thr Cys Cys Phe Asn Val
 1               5                  10                  15
Ile Asn Arg Lys Ile Pro Ile Gln Arg Leu Glu Ser Tyr Thr Arg Ile
                20                  25                  30
Thr Asn Ile Gln Cys Pro Lys Glu Ala Val Ile Phe Lys Thr Lys Arg
                35                  40                  45
Gly Lys Glu Val Cys Ala Asp Pro Lys Glu Arg Trp Val Arg Asp Ser
        50                  55                  60
Met Lys His Leu Asp Gln Ile Phe Gln Asn Leu Lys Pro
65                  70                  75
```

( 2 ) INFORMATION FOR SEQ ID NO:10:

( i ) SEQUENCE CHARACTERISTICS:
    ( A ) LENGTH: 92 amino acids
    ( B ) TYPE: amino acid
    ( C ) STRANDEDNESS: single
    ( D ) TOPOLOGY: linear ( i i ) MOLECULE TYPE: peptide ( v i i ) IMMEDIATE SOURCE:
    ( A ) LIBRARY: GENBANK (B) CLONE: GI 127078

(xi) SEQUENCE DESCRIPTION: SEQ ID NO:10:

| Met | Gln | Val | Ser | Thr | Ala | Ala | Leu | Ala | Val | Leu | Leu | Cys | Thr | Met | Ala |
|---|---|---|---|---|---|---|---|---|---|---|---|---|---|---|---|
| 1 | | | | 5 | | | | | 10 | | | | | 15 | |

| Leu | Cys | Asn | Gln | Phe | Ser | Ala | Ser | Leu | Ala | Ala | Asp | Thr | Pro | Thr | Ala |
|---|---|---|---|---|---|---|---|---|---|---|---|---|---|---|---|
| | | | 20 | | | | | 25 | | | | | 30 | | |

| Cys | Cys | Phe | Ser | Tyr | Thr | Ser | Arg | Gln | Ile | Pro | Gln | Asn | Phe | Ile | Ala |
|---|---|---|---|---|---|---|---|---|---|---|---|---|---|---|---|
| | | 35 | | | | | 40 | | | | | 45 | | | |

| Asp | Tyr | Phe | Glu | Thr | Ser | Ser | Gln | Cys | Ser | Lys | Pro | Gly | Val | Ile | Phe |
|---|---|---|---|---|---|---|---|---|---|---|---|---|---|---|---|
| | 50 | | | | | 55 | | | | | 60 | | | | |

| Leu | Thr | Lys | Arg | Ser | Arg | Gln | Val | Cys | Ala | Asp | Pro | Ser | Glu | Glu | Trp |
|---|---|---|---|---|---|---|---|---|---|---|---|---|---|---|---|
| 65 | | | | | 70 | | | | | 75 | | | | | 80 |

| Val | Gln | Lys | Tyr | Val | Ser | Asp | Leu | Glu | Leu | Ser | Ala |
|---|---|---|---|---|---|---|---|---|---|---|---|
| | | | | 85 | | | | | 90 | | |

(2) INFORMATION FOR SEQ ID NO:11:

(i) SEQUENCE CHARACTERISTICS:
     (A) LENGTH: 92 amino acids
     (B) TYPE: amino acid
     (C) STRANDEDNESS: single
     (D) TOPOLOGY: linear (ii) MOLECULE TYPE: peptide (vii) IMMEDIATE SOURCE:
     (A) LIBRARY: GENBANK
     (B) CLONE: GI 127080

(xi) SEQUENCE DESCRIPTION: SEQ ID NO:11:

| Met | Lys | Leu | Cys | Val | Thr | Val | Leu | Ser | Leu | Leu | Met | Leu | Val | Ala | Ala |
|---|---|---|---|---|---|---|---|---|---|---|---|---|---|---|---|
| 1 | | | | 5 | | | | | 10 | | | | | 15 | |

| Phe | Cys | Ser | Pro | Ala | Leu | Ser | Ala | Pro | Met | Gly | Ser | Asp | Pro | Pro | Thr |
|---|---|---|---|---|---|---|---|---|---|---|---|---|---|---|---|
| | | | 20 | | | | | 25 | | | | | 30 | | |

| Ala | Cys | Cys | Phe | Ser | Tyr | Thr | Ala | Arg | Lys | Leu | Pro | Arg | Asn | Phe | Val |
|---|---|---|---|---|---|---|---|---|---|---|---|---|---|---|---|
| | | 35 | | | | | 40 | | | | | 45 | | | |

| Val | Asp | Tyr | Tyr | Glu | Thr | Ser | Ser | Leu | Cys | Ser | Gln | Pro | Ala | Val | Val |
|---|---|---|---|---|---|---|---|---|---|---|---|---|---|---|---|
| | 50 | | | | | 55 | | | | | 60 | | | | |

| Phe | Gln | Thr | Lys | Arg | Ser | Lys | Gln | Val | Cys | Ala | Asp | Pro | Ser | Glu | Ser |
|---|---|---|---|---|---|---|---|---|---|---|---|---|---|---|---|
| 65 | | | | | 70 | | | | | 75 | | | | | 80 |

| Trp | Val | Gln | Glu | Tyr | Val | Tyr | Asp | Leu | Glu | Leu | Asn |
|---|---|---|---|---|---|---|---|---|---|---|---|
| | | | | 85 | | | | | 90 | | |

(2) INFORMATION FOR SEQ ID NO:12:

(i) SEQUENCE CHARACTERISTICS:
     (A) LENGTH: 91 amino acids
     (B) TYPE: amino acid
     (C) STRANDEDNESS: single
     (D) TOPOLOGY: linear (ii) MOLECULE TYPE: peptide (vii) IMMEDIATE SOURCE:
     (A) LIBRARY: GENBANK
     (B) CLONE: GI 134510

(xi) SEQUENCE DESCRIPTION: SEQ ID NO:12:

| Met | Lys | Val | Ser | Ala | Ala | Arg | Leu | Ala | Val | Ile | Leu | Ile | Ala | Thr | Ala |
|---|---|---|---|---|---|---|---|---|---|---|---|---|---|---|---|
| 1 | | | | 5 | | | | | 10 | | | | | 15 | |

| Leu | Cys | Ala | Pro | Ala | Ser | Ala | Ser | Pro | Tyr | Ser | Ser | Asp | Thr | Thr | Pro |
|---|---|---|---|---|---|---|---|---|---|---|---|---|---|---|---|
| | | | 20 | | | | | 25 | | | | | 30 | | |

| | | | | | | | | | | | | | | |
|---|---|---|---|---|---|---|---|---|---|---|---|---|---|---|
| Cys | Cys | Phe<br>35 | Ala | Tyr | Ile | Ala | Arg<br>40 | Pro | Leu | Pro | Arg | Ala<br>45 | His | Ile | Lys |
| Glu | Tyr<br>50 | Phe | Tyr | Thr | Ser | Gly<br>55 | Lys | Cys | Ser | Asn | Pro<br>60 | Ala | Val | Val | Phe |
| Val<br>65 | Thr | Arg | Lys | Asn | Arg<br>70 | Gln | Val | Cys | Ala | Asn<br>75 | Pro | Glu | Lys | Lys | Trp<br>80 |
| Val | Arg | Glu | Tyr | Ile<br>85 | Asn | Ser | Leu | Glu | Met<br>90 | Ser | | | | | |

We claim:

1. A recombinant DNA molecule comprising DNA encoding liver expressed chemokine (LVEC-1) of amino acid sequence shown in SEQ ID NO: 2.

2. The recombinant DNA molecule of claim 1 wherein the nucleotide sequence comprises SEQ ID NO: 1, or its complement.

3. An expression vector comprising the DNA molecule of claim 1.

4. A host cell transformed with the expression vector of claim 3.

5. A method for producing the liver expressed chemokine polypeptide (LVEC-1), said method comprising the steps:
   a) culturing the host cells of claim 4 under conditions suitable for the expression of LVEC-1; and
   b) recovering LVEC-1 from the cell culture.

* * * * *

UNITED STATES PATENT AND TRADEMARK OFFICE
CERTIFICATE OF CORRECTION

PATENT NO. : 5,602,008
DATED : February 11, 1997
INVENTOR(S) : Craig G. Wilde, Phillip R. Hawkins, Olga Bandman, Jeffrey J. Seilhamer Page 1 of 1

It is certified that error appears in the above-identified patent and that said Letters Patent is hereby corrected as shown below:

Column 29,
Line 15, delete "A recombinant" and insert --An isolated recombinant--

Signed and Sealed this

Third Day of July, 2001

*Attest:*

Nicholas P. Godici

*Attesting Officer*

NICHOLAS P. GODICI
*Acting Director of the United States Patent and Trademark Office*